(12) United States Patent  
Miyachi

(10) Patent No.: US 9,826,959 B2  
(45) Date of Patent: Nov. 28, 2017

(54) ULTRASONIC DIAGNOSTIC DEVICE

(75) Inventor: Yukiya Miyachi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1763 days.

(21) Appl. No.: 12/588,904

(22) Filed: Nov. 2, 2009

(65) Prior Publication Data

US 2010/0113930 A1 May 6, 2010

(30) Foreign Application Priority Data

Nov. 4, 2008 (JP) ................................. 2008-283280  
Nov. 25, 2008 (JP) ................................. 2008-299256  
Nov. 27, 2008 (JP) ................................. 2008-302049  
Mar. 31, 2009 (JP) ................................. 2009-087787

(51) Int. Cl.

| A61B 8/00 | (2006.01) |
|---|---|
| A61B 8/08 | (2006.01) |
| A61B 5/02 | (2006.01) |
| A61B 5/022 | (2006.01) |
| A61B 5/00 | (2006.01) |

(52) U.S. Cl.

CPC ............ *A61B 8/0858* (2013.01); *A61B 5/022* (2013.01); *A61B 5/02007* (2013.01); *A61B 5/7275* (2013.01); *A61B 8/485* (2013.01); *A61B 8/486* (2013.01)

(58) Field of Classification Search

CPC ... A61B 5/02007; A61B 5/022; A61B 5/7275; A61B 8/0858; A61B 8/485  
USPC ....................................................... 600/438  
See application file for complete search history.

(56) References Cited

U.S. PATENT DOCUMENTS

| 6,012,458 A | * | 1/2000 | Mo | ........................ | G03B 42/06 |
|---|---|---|---|---|---|
| | | | | | 128/916 |
| 6,106,470 A | * | 8/2000 | Geiser | .................... | G03B 42/06 |
| | | | | | 128/916 |

(Continued)

FOREIGN PATENT DOCUMENTS

| JP | 06-058958 A | 3/1994 |
|---|---|---|
| JP | 08-140974 | 6/1996 |
| JP | 08-292791 A | 11/1996 |
| JP | 10-071147 | 3/1998 |

(Continued)

*Primary Examiner* — James Kish  
(74) *Attorney, Agent, or Firm* — Edwards Neils LLC; Jean C. Edwards, Esq.

(57) ABSTRACT

An ultrasonic diagnostic device includes: a transmission and reception circuit that processes reception signals output from an ultrasonic probe to generate reception data; a memory that stores the reception data; an image data generation portion that generates B-mode image data and M-mode image data based on the reception data; a detection portion that detects hand movement or body movement in the reception data; a determination portion that detects an amount of change of a relative position between the ultrasonic probe and a body under test in the reception data in which the hand movement or the body movement is detected, and determine an accuracy of the reception data; and an elastic characteristic calculation portion that measures a displacement magnitude of a living body tissue in the reception data determined by the determination portion to be highly accurate, and calculates elastic characteristic by using the displacement magnitude.

8 Claims, 32 Drawing Sheets

(9 of 32 Drawing Sheet(s) Filed in Color)

(56) References Cited

U.S. PATENT DOCUMENTS

| | | | |
|---|---|---|---|
| 6,589,176 B2* | 7/2003 | Jago | A61B 8/00 600/443 |
| 8,699,765 B2* | 4/2014 | Hao | A61B 8/00 600/443 |
| 2003/0105401 A1* | 6/2003 | Jago | A61B 8/00 600/443 |
| 2004/0066398 A1* | 4/2004 | Dolimier | A61B 8/463 715/720 |
| 2004/0111028 A1* | 6/2004 | Abe | A61B 8/488 600/437 |
| 2007/0032726 A1* | 2/2007 | Osaka | A61B 5/0048 600/459 |
| 2007/0232925 A1* | 10/2007 | Satoh | 600/459 |
| 2009/0270730 A1* | 10/2009 | Azuma | A61B 8/0833 600/443 |

FOREIGN PATENT DOCUMENTS

| | | |
|---|---|---|
| JP | 2002-209857 A | 7/2002 |
| JP | 3464185 | 8/2003 |
| JP | 2005-052424 A | 3/2005 |
| JP | 2006-055266 A | 3/2006 |
| JP | 2006-521146 | 9/2006 |
| JP | 3882084 | 11/2006 |
| JP | 2007-006914 | 1/2007 |
| JP | 2007-312958 | 12/2007 |
| JP | 4091365 | 3/2008 |
| JP | 2008-237670 A | 10/2008 |
| WO | WO 03/015635 | 2/2003 |
| WO | WO 2004/086082 | 10/2004 |
| WO | WO 2005/002446 A1 | 1/2005 |
| WO | WO 2006/068079 | 6/2006 |
| WO | WO 2006/132203 A1 | 12/2006 |

* cited by examiner

603 BLOOD VESSEL FRONT WALL

604 VASCULAR LUMEN

605 BLOOD VESSEL REAR WALL

NORMAL EXAMPLE

MT LARGE THICKNESS EXAMPLE

FRAME B MODE IMAGE

NO EXISTENCE

FRAME B MODE IMAGE

LINE A M MODE IMAGE

LINE B M MODE IMAGE

ULTRASONIC DIAGNOSTIC DEVICE

CROSS-REFERENCE TO RELATED APPLICATIONS

The present application claims priority from Japanese Patent Application No. 2008-283280, filed Nov. 4, 2008, Japanese Patent Application No. 2008-299256, filed Nov. 25, 2008, Japanese Patent Application No. 2008-302049, filed Nov. 27, 2008 and Japanese Patent Application No. 2009-87787, filed Mar. 31, 2009, the contents of which are herein incorporated by reference in their entirety.

BACKGROUND OF THE INVENTION

Field of the Invention

The present invention relates to an ultrasonic diagnostic device that has the function of simultaneously displaying the measurement results of the intima media thickness (IMT) and the elastic indices of a blood vessel to allow the risk of arteriosclerosis to be easily determined. The present invention also relates to an ultrasonic diagnostic device that visually displays variations in measurement results, and more particularly relates to an ultrasonic diagnostic device that displays, in an easily understandable manner, the change of the blood vessel wall or the like of a carotid artery to allow the condition of a plaque or the like to be easily determined. The present invention also relates to an ultrasonic diagnostic device that stably acquires the elastic indices of a blood vessel or the like to display them. The present invention also relates to an ultrasonic diagnostic device that can measure elastic indices, and more particularly relates to an ultrasonic diagnostic device that detects handshake or body shake to allow unstable data to be reliably removed from acquired ultrasonic image information and that can measure elastic indices.

Description of a Related Art

In recent years, patients that are treated for a cardiocirculatory disease like an ischemia disease such as cerebral infarction, cardiac infarction or angina pector have been rapidly increasing. In order to prevent these diseases, it is important to notice an early sign of arteriosclerosis to improve daily habits; the Ministry of Health, Labor and Welfare introduces schemes such as mandatory metabolic syndrome checkups.

As common methods of noninvasively measuring the condition of arteriosclerosis, there are pulse wave velocity (PWV) measurement and intima media thickness (IMT) measurement using the echo of a carotid artery; the clinical diagnostic values thereof have been obvious.

The IMT refers to, among an arterial wall having a three-layer structure composed of an intima, a media and an adventitia, the total thickness of the intima and the media (specifically, a length from the boundary between a vascular lumen and the intima to the boundary between the media and the adventitia). Recent research is showing that, as arteriosclerosis progresses, the intima media thickness is increased and plaque is formed. Here, the plaque refers to a portion that is formed by the inward expansion of a blood vessel wall. The tissue of the plaque is composed of various things such as a blood clot and an adipose or fiber tissue, and flaked plaque is responsible for the coarctation of a carotid artery, brain ischemia and the like.

The IMT can be measured by ultrasonic examination (carotid artery ultrasonic examination). Specifically, an ultrasound probe is pressed onto the neck of a body under test (patient), and ultrasound is sent from the ultrasound probe. Since the ultrasound is reflected off the surface (the boundary between different tissues) of the structure of the body under test, the resulting ultrasonic echo is received by the ultrasound probe, and, based on the received signal, an ultrasonic image is generated. Here, the IMT of a carotid artery is measured because, in the regions of the carotid artery, such as a blood vessel branch portion between an external carotid artery connected to the artery of a face and an internal carotid artery connected to a cerebral artery and a portion for receiving blood for the carotid artery, where the direction of blood flow changes, plaque is more likely to be formed, and because the carotid artery is the favorite site of arteriosclerosis.

FIG. 36 is an example of an ultrasonic image showing a normal blood vessel wall; FIG. 37 is an example of an ultrasonic image showing a blood vessel wall in which the thickness of its membrane is increased by plaque. The boundary of the blood vessel wall is determined from the generated ultrasonic image, and the thickness is measured with a vernier caliper or the like, with the result that the IMT can be obtained. Moreover, an examiner (an operator such as a doctor) diagnoses the state of arteriosclerosis based on the IMT, and, based on the results, estimates the degree of blood vessels in a whole body including a heart and a brain.

FIG. 38 is a graph that is presented by O'Leary D H et al. and that shows the relationship between the IMT and a cerebral stroke risk rate. The IMT is obviously correlated with the cerebral stroke risk rate, and the graph shows that, when the IMT is 1.1 mm or more, the cerebral stroke risk rate rapidly increases.

However, since the IMT is an index showing only the morphological change of a carotid artery, but not the dynamic characteristic of a blood vessel, it is not appropriate to evaluate the degree of arteriosclerosis with the IMT alone.

On the other hand, the pulse wave velocity (PWV) is a velocity obtained by measuring a heart when it contracts, detecting the pulse waves of a carotid artery and a femoral artery from a body surface and calculating the spread time from the contraction of the heart to the generation of the pulse wave, and serves as a parameter showing the hardness of an artery. With the PWV, it is possible to quantitatively diagnose the progress of arteriosclerosis and estimate the age of a blood vessel or the like. Since preventive medicine is considered to be important, attention is given to the PWV as a new preventive medicine index showing the dynamic characteristic of a blood vessel.

In recent years, diagnostic apparatuses for easily measuring the PWV from the pulse waves of an arm and an ankle have been commercially available. There is provided an instrument that displays a cardio ankle vascular index (CAVI) for presenting, by measuring the PWV, a stiffness parameter β that is the elastic coefficient of a blood vessel.

FIG. 39 is a graph that is presented by FURUHASHI Hiroshi et al. and that shows variations in stiffness parameter β on an age-by-age basis. The graph shows that, irrespective of male or female, as the age increases, the stiffness parameter β increases.

Methods for determining elastic indices such as a stiffness parameter β, a blood vessel diameter variation rate and an elastic modulus have been developed by calculating the displacement of a blood vessel wall from the echo of a carotid artery, and thus the applications thereof to diagnoses are expected. It is said that variations in elastic indices are produced before the morphological change of the IMT, and it is thus expected that this facilitates the early detection of arteriosclerosis.

In patent document 1, there is disclosed a method for determining the age of a blood vessel from only moving images of expansion-contraction deformation. In the disclosed method, for example, a value obtained by dividing the difference of a blood vessel diameter between when an artery is most expanded and when it is most contracted by the blood vessel diameter when the artery is most expanded is divided by the time difference, and the resulting value is obtained as an arteriosclerosis factor; comparison information with respect to a plurality of males and females and based on the correlation between their ages and arteriosclerosis factors is collected and stored; the arteriosclerosis factors of the persons to be tested are determined, to what degree the arteriosclerosis factors are different from the average arteriosclerosis factors of the persons of the same age is expressed as percentage and the resulting value is obtained as an age standard ratio; and the diagnostic results of the persons to be tested are represented by this age standard ratio. The degree of arteriosclerosis is compared with that of the average person of the same age, and this results in the effect of improving the recognition of the risk of arteriosclerosis to enhance the motivation of improving the daily habits. FIG. 40 is a graph that is shown in patent document 1 and that shows the correlation between arteriosclerosis factors serving as a parameter representing the mechanical characteristic of an artery and ages. This graph clearly shows that the arteriosclerosis factors depend on ages.

In patent document 2, there is disclosed a device that produces a tomographic image of a blood vessel with ultrasound, that computes the displacement of a blood vessel wall on a measurement line, that computes a blood flow rate at a sample gate with respect to the measurement line and that, from these results, computes a wave intensity WI. The WI serves as an index for determining which action is predominant, the action of forward pulse waves moving from a heart to peripheries or the action of reflected pulse waves moving from the peripheries to the heart; the WI is determined as the product of the amount of change in a pressure on a localized portion of an artery and the amount of change in a blood flow rate during a predetermined period of time or the product of the time-derivative value of a blood pressure on the localized portion and the time-derivative value of the blood flow rate. The WI can be utilized as elastic indices of a blood vessel for evaluating the characteristics of the blood vessel, the functions of a heart and the like.

In patent document 3, there is disclosed an ultrasonic diagnostic device that utilizes the stiffness parameter $\beta$ to determine the blood pressure of a localized portion. The stiffness parameter $\beta$ is a factor related to variations in blood pressure within a blood vessel and variations in blood vessel cross-sectional area or blood vessel diameter; the stiffness parameter $\beta$ is a blood vessel index for showing the hardness of a blood vessel.

Although it is found that the IMT showing the morphological change of a blood vessel and the parameter (elastic index) showing the hardness of a blood vessel are each positively correlated with arteriosclerosis, the correlation does not always hold true. Specifically, there is a patient who has a thin IMT but an unevenly dynamic change of a blood vessel or, in contrast, a patient who has a thick IMT but a highly dynamic change of a blood vessel. Thus, it is impossible to correctly estimate the risk for the development of arteriosclerosis either by the diagnosis of the IMT or the diagnosis of the elastic index showing the dynamic characteristic of a blood vessel, with the result that it is necessary to observe the both of them in a composite manner.

[Patent document 1] Japanese Patent No. 3882084
[Patent document 2] Japanese Patent No. 3464185
[Patent document 3] Japanese Patent No. 4091365

Generally, when the IMT becomes thick, it is possible to determine the condition in the early stage of arteriosclerosis, and when plaque is produced, to determine the condition to be more advanced. As employed in non-patent document 1 published by the Japan Society of Ultrasonics in Medicine, a method is established of measuring the thickness of plaque or the degree of the narrowing to determine the risk of arteriosclerosis.

In recent years, it has become obvious that, in cerebral infarction, ischemic cardiac disease and the like, not only the degree of the narrowing but also the ease of the tear of plaque are problematic. In patent document 4, there is disclosed an advanced method of measuring, from the slight displacement of a blood vessel wall, variations in thickness to determine an elastic modulus, identifying the type of a body tissue and thus performing a rapid diagnosis.

As described above, methods have been developed of calculating the displacement of a blood vessel wall to determine elastic indices, such as a stiffness parameter $\beta$, a strain and an elastic modulus, that shows the state of a blood vessel. However, these elastic indices involve, for example, the following problems: (a) it is necessary to track the slight displacement of a moving blood vessel wall; (b) a probe is likely to be displaced from an observed location due to the hand shake of an operator and the body movement of a person to be tested; and (c) when it is impossible to obtain a clear image due to the person to be tested or the like, it is difficult to obtain highly reproducible data. The main reason for the failure to obtain stable data is that variations in brightness information or phase information, noise in the form of a spike that is abruptly produced or the like cause erroneous tracking.

In patent document 5, there is disclosed a technology in which, in order for an appropriate elastic image for use in diagnosis to be displayed, an error of the elastic image is evaluated with the brightness information of a tomographic image and error information is displayed. The elastic image within an error region may be deleted. In patent document 6, there is disclosed an ultrasonic diagnostic device that is provided with a calculation portion for determining a characteristic value (an elastic modulus) over time, a stability determination portion for sequentially determining the stability and an expression portion for expressing the stability.

In patent document 7, there is disclosed a method in which a thickness variation waveform showing variations in distance between measured regions is compared with a reference waveform, an index showing the degree of agreement is calculated and the amount of variation of the maximum thickness and the reliability of an elastic modulus are determined.

As described above, various inventions are disclosed that distinguish between the stable data and the error data so that an operator can obtain reliable data; however, in fact, required accuracy in an operation is disadvantageously high, and the operator is not satisfied with such determination. Moreover, disadvantageously, from the obtained values on a stiffness parameter $\beta$, a strain and an elastic modulus, it is difficult for an examiner such as a doctor to visually image and understand the movement state.

On the other hand, as a method of measuring, with an ultrasonic diagnostic device, the displacement of a tissue, M mode display has been known for a long time. In this method, the temporal change of a tissue on a line of interest can be easily recognized but there is a problem in which the method is not appropriate for observing the movement of the entire tissue.

Furthermore, in patent document 8, there is disclosed a three-dimensional ultrasonic imaging system; it can three-dimensionally display the position of a tissue but it cannot facilitate the three-dimensionally imaging and the understanding of the temporal change of a tissue.

[Patent document 4] WO 2003/015635
[Patent document 5] JP-A-2007-312958
[Patent document 6] WO 2006/068079
[Patent document 7] JP-A-2007-006914
[Patent document 8] JP-T-2006-521146

[Non-patent document 1] "A standard method of evaluating the lesion of a carotid artery by ultrasonic (proposal)" published in "Jpn J Med Ultrasonics", Vol. 35, No. 2, p. 202-209, in June, 2008

FIG. 41 is a diagram showing an ultrasonic image of a carotid artery. A vascular lumen intima boundary and a media adventitia boundary in a blood vessel wall are determined from a generated ultrasonic image, and the length between both the boundaries is measured with a vernier caliper or the like, with the result that an IMT can be determined. Moreover, an examiner (an operator such as a doctor) diagnoses, based on the IMT, the degree of arteriosclerosis, and can estimate, based on the result, the state of blood vessels in the entire body including a heat and a brain.

Here, the IMT of the carotid artery is measured because, in regions such as a blood vessel branch portion between an external carotid artery connected to the artery of a face and an internal carotid artery connected to a cerebral artery and a portion for receiving blood for the carotid artery, where the direction of blood flow changes, plaque is more likely to be formed, and because the carotid artery is the favorite site of arteriosclerosis.

FIGS. 42A and 42B and FIGS. 43A and 43B are diagrams showing images for measuring a minute displacement of a carotid artery blood vessel wall with an ultrasonic probe shown in FIG. 44 pressed onto a neck. In the ultrasonic probe shown in FIG. 44, an arrangement vibrator is used in which square bar-shaped vibrators are linearly arranged. The ultrasonic probe having such a configuration can perform, without moving the probe itself, linear scanning by moving the position of an ultrasonic beam, that is, a scanning line in a direction perpendicular to a direction of the beam.

Generally, in an ultrasonic diagnostic device, ultrasound output from a vibrator in an ultrasonic probe is enhanced and modulated by a body under test, and the strength of the resulting ultrasonic echo is spread in a scanning width direction and displayed and thus an image is obtained; this image is referred to as a "B mode image". An attention is paid to a certain portion of the body under test, and temporal changes in sound waves reflected here are spread and displayed and thus an image is obtained; this image is referred to as an "M mode".

FIGS. 42A and 42B are diagrams showing examples of the B mode image. FIG. 42A shows an image in an i-frame; FIG. 42B shows an image in a j-frame. In these B mode images, a line A and a line B are indicated by arrows.

FIGS. 43A and 43B are diagrams showing examples of the M mode image in which echo produced in a constant beam direction by use of the same measurement result as described above is displayed over time. FIG. 43A shows an image acquired in the line A; FIG. 43B shows an image acquired in the line B. In these M mode images, the i-frame and the j-frame are indicated by arrows.

In the examples shown in FIGS. 42A and 42B and FIGS. 43A and 43B, in the line A, data could be stably acquired not only in the i-frame but also in the j-frame; however, in the line B, since the image of a blood vessel wall was unstable due to variations in brightness information and phase, data could not be acquired stably, and tracking resulted in failure, with the result that it was impossible to measure elastic indices stably. Thus, it is necessary to perform tracking on the line showing stable dada appearing on the B mode image and to use the data acquired by the tracking to determine elastic indices.

On the other hand, when the displacement of a tissue is measured with an ultrasonic diagnostic device, a method has been known for a long time of performing an M mode measurement in the ultrasonic echo inspection of a carotid artery to measure the displacement of a blood vessel in synchronization with cardiac pulsation. In patent document 9, there is disclosed a method in which, from the minute displacement of a blood vessel wall, the variation of its thickness is measured and thus an elastic modulus is determined, and the type of a body tissue is identified, with the result that a rapid diagnosis is performed. Moreover, in the non-patent document 1, as an item for evaluating arteriosclerosis lesion, the measurement of the IMT and an artery diameter is described, and it is suggested that the measurement of an artery diameter be performed with the M mode through a cross-sectional image of the pulsating artery in either the maximum diameter time phase or the minimum diameter time phase.

Advantageously, in the diagnosis using the M mode image, it is needless to say that a doctor or the like is used to using it, a doctor or the like can determine, on inspection, whether to acquire the M mode image stably, and, if the M mode image is not stably measured, it is possible to measure it again there. However, the diagnosis using the M mode image is not suitable for quantitatively measuring the minute displacement of movement of a blood vessel wall because, for example, the scale in image range is too different.

[Patent document 9] JP-A-H10-71147

In patent document 10, there is disclosed an ultrasonic diagnostic device that is provided with hand shake detection means for performing resetting if detecting hand shake in a color Doppler blood flow maximum value overwrite mode; however, it discloses no further specific information such as a detection method.

As described above, various inventions are disclosed that determine stable data and error data to allow an operator to acquire reliable data; however, in fact, the accuracy required for calculating elastic indices is too high, and thus the operator is not satisfied with the determination, with the result that the major problem is encountered in stably acquiring elastic indices.

[Patent document 10] JP-A-H08-140974

SUMMARY OF THE INVENTION

Problems to be Solved by the Invention

In one aspect of the present invention, an object is to provide an ultrasonic diagnostic device that simultaneously displays an IMT and the elastic indices of a blood vessel to accurately determine, through composite observations, the risk for developing arteriosclerosis.

In another aspect of the present invention, an object is to provide an ultrasonic diagnostic device that edits ultrasonic image signals to visually display a movement state in a region to be measured in an easily understandable manner.

In another aspect of the present invention, an object is to provide an ultrasonic diagnostic device that accurately removes unstable data from acquired ultrasonic image information to calculate and display proper elastic indices.

In another aspect of the present invention, an object is to provide an ultrasonic diagnostic device that accurately removes unstable data from ultrasonic image information acquired by detecting hand shake or body shake and that can measure elastic indices.

According to one aspect of the present invention, there is provided an ultrasonic diagnostic device including: an ultrasonic probe that transmits ultrasound to a body under test and that receives ultrasonic echo reflected off the body under test to output a reception signal; image data generation means that generates, based on the reception signal output from the ultrasonic probe, image data representing an ultrasonic image on a blood vessel of the body under test; IMT measurement means that measures, based on the image data generated by the image data generation means, an IMT (intima media thickness) of the blood vessel; elastic index measurement means that determines, based on the image data generated by the image data generation means, a value representing an elastic index of the blood vessel; and display means that displays a two-dimensional coordinate system in which the IMT is represented on a first coordinate axis and the value representing the elastic index of the blood vessel is represented on a second coordinate axis.

According to another aspect of the present invention, there is provided an ultrasonic diagnostic device including: an ultrasonic probe that transmits ultrasound to a body under test and that receives ultrasonic echo reflected off the body under test to output a reception signal; image data generation means that generates, based on the reception signal output from the ultrasonic probe, image data representing an ultrasonic image of the body under test along a measurement line which is set; subject setting means that sets a subject region to be measured in the ultrasonic image represented by the image data; position identifying means that measures, from the ultrasonic image, a distance in a vertical direction in a measurement position in the subject region to be measured; display processing means that generates a screen displaying temporal changes in the subject region to be measured in a three-dimensional coordinate system in which the measurement position in the subject region to be measured is represented on a first axis, the distance in the vertical direction at the measurement position is represented on a second axis and time is represented on a third axis; and a display device that displays the screen.

According to another aspect of the present invention, there is provided an ultrasonic diagnostic device including: transmit/receive means that supplies a plurality of drive signals to an ultrasonic probe including a plurality of ultrasonic transducers transmitting and receiving ultrasound and that processes a plurality of reception signals output from the ultrasonic probe to generate reception data; storage means that stores the reception data generated by the transmit/receive means; image data generation means that generates, based on the reception data stored in the storage means, B mode image data representing a B mode image and that reads, based on one or a plurality of lines of interest set at one or a plurality of positions in the B mode image, a characteristic amount from the reception data stored in the storage means to generate M mode image data representing one or a plurality of M mode images; and elastic index calculation means that calculates an elastic index with the reception data corresponding to the M mode image selected from the one or the plurality of M mode images.

According to another aspect of the present invention, there is provided an ultrasonic diagnostic device including: an ultrasonic probe that includes a plurality of ultrasonic transducers transmitting and receiving ultrasound to and from a body tissue moving in synchronization with a pulse of a body under test; transmit/receive means that supplies a plurality of drive signals to the ultrasonic probe and that processes a plurality of reception signals output from the ultrasonic probe to generate reception data; storage means that stores the reception data generated by the transmit/receive means; image data generation means that generates, based on the reception data stored in the storage means, the reception data corresponding to a B mode image and that reads a characteristic amount from the reception data stored in the storage means to generate the reception data corresponding to one or a plurality of M mode images; detection means that detects hand shake or body shake with the reception data corresponding to the M mode image generated by the image data generation means; determination means that uses the reception data corresponding to the M mode image in which the hand shake or the body shake is detected by the detection means to detect an amount of variation of a relative position between the ultrasonic probe and the body under test, and that determines, with the amount of variation, an accuracy of the reception data corresponding to the M mode image; and elastic characteristic calculation means that measures, with the reception data corresponding to the M mode image selected from the one or the plurality of M mode images determined by the determination means to be highly accurate, an amount of displacement of the body tissue, and that calculates the elastic characteristic with the amount of displacement.

According to another aspect of the present invention, there is provided an ultrasonic diagnostic device including: an ultrasonic probe that includes a plurality of ultrasonic transducers transmitting and receiving ultrasound to and from a body tissue moving in synchronization with a pulse of a body under test; transmit/receive means that supplies a plurality of drive signals to the ultrasonic probe and that processes a plurality of reception signals output from the ultrasonic probe to generate reception data; storage means that stores the reception data generated by the transmit/receive means; image data generation means that generates, based on the reception data stored in the storage means, the reception data corresponding to a B mode image and that reads a characteristic amount from the reception data stored in the storage means to generate the reception data corresponding to one or a plurality of M mode images; elastic characteristic calculation means that measures, with the reception data corresponding to the M mode image selected from the reception data corresponding to the one M mode image or the reception data corresponding to the plurality of M mode images, an amount of displacement of the body tissue, and that calculates the elastic characteristic from the amount of displacement; detection means that detests, with the reception data corresponding to the M mode image selected, hand shake or body shake; and determination means that uses the reception data corresponding to the M mode image in which the hand shake or the body shake is detected by the detection means to detect an amount of variation of a relative position between the ultrasonic probe and the body under test, and that determines, with the amount of variation, an accuracy of the elastic characteristic calculated by the elastic characteristic calculation means.

Preferably, in the ultrasonic diagnostic device according to another aspect of the present invention, the detection means detects, with the reception data corresponding to both the M mode image and the body tissue between the ultrasonic probe when the ultrasonic probe is pressed onto the body under test and an area where the elastic characteristic is calculated, the hand shake or the body shake.

Preferably, in the ultrasonic diagnostic device according to another aspect of the present invention, when the determination means uses the amount of variation to determine the accuracy, a beat in which the amount of variation of the relative position is larger than a threshold is determined to be less accurate.

In the ultrasonic diagnostic device according to another aspect of the present invention, the amount of variation of the relative position in the determination means can also be detected by a difference image between frames of the M mode image or a pattern matching method.

In the ultrasonic diagnostic device according to another aspect of the present invention, the amount of variation of the relative position detected by the determination means is subtracted from the amount of displacement of the body tissue measured by the elastic characteristic calculation means, and thus the ultrasonic diagnostic device has a function of correcting the amount of displacement of the body tissue, and the elastic characteristic calculation means can calculate the elastic characteristic with the amount of displacement of the body tissue corrected by the function.

According to one aspect of the present invention, since the IMT and the elastic indices of a blood vessel obtained based on image data representing an ultrasonic image on the blood vessel are displayed together in a two-dimensional coordinate system, it is possible to observe the IMT and the elastic indices of the blood vessel in a composite manner to accurately determine arteriosclerosis risk.

According to another aspect of the present invention, since, based on the data of a plurality of sheets of ultrasonic images obtained, the variation of the images is three-dimensionally displayed in a three-dimensional coordinate system in which one axis is a time axis, it is possible to visually and easily understand the movement state of a subject region to be measured. In particular, when a display method according to another aspect of the present invention is applied to an ultrasonic tomographic image of a carotid artery, it is possible to accurately estimate not only the shape but also the characteristic of plaque formed inside a blood vessel and to more accurately determine arteriosclerosis risk.

According to another aspect of the present invention, one or a plurality of B mode images formed from stored reception data are displayed, based on one or a plurality of lines of interest set by selecting a position where a stable measurement signal is obtained, a characteristic amount is read from the stored reception data, and an M mode image is displayed, and a preferred M mode image is specified from the M mode image, and then, based on a measurement value obtained on the reception data corresponding to the M mode image, an elastic index is determined. Thus, with the ultrasonic diagnostic device of the present invention, since a satisfactory data region is selected from displayed image data, and can be utilized as an elastic index, it is possible to obtain a stable elastic index.

According to another aspect of the present invention, there is provided an ultrasonic diagnostic device that can measure an elastic index in which unstable data can be reliably removed from ultrasonic image information acquired by detecting hand shake or body hake.

The patent or application file contains at least one drawing executed in color. Copies of this patent or patent application publication with color drawing(s) will be provided by the Office upon request and payment of the necessary fee.

DESCRIPTION OF THE PREFERRED EMBODIMENTS

Embodiments of the present invention will be described in detail below with reference to the accompanying drawings.

First Embodiment

Figure 1:
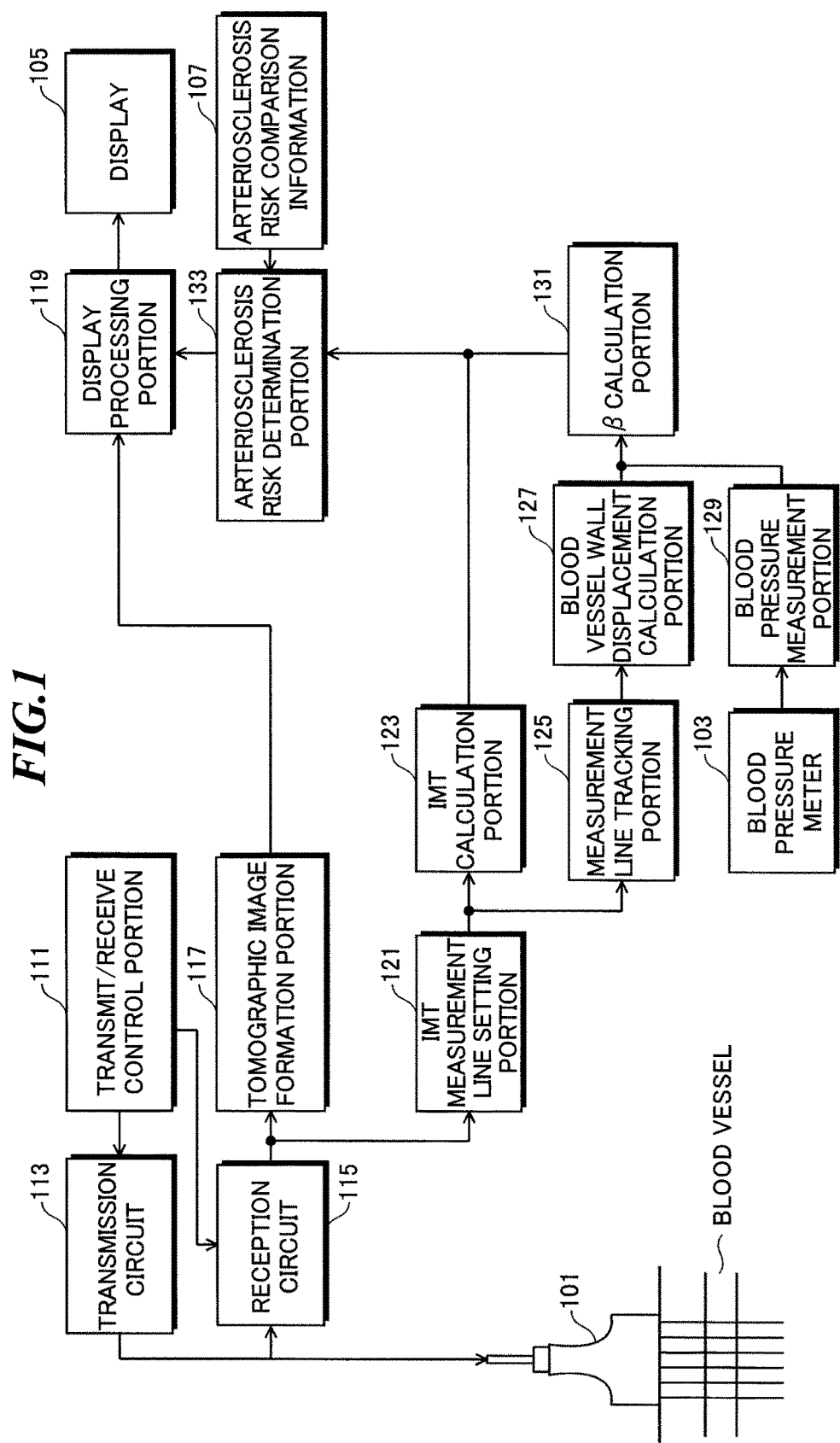
FIG. 1 is a block diagram showing the configuration of an ultrasonic diagnostic device according to a first embodiment of the present invention.
Figure 2:
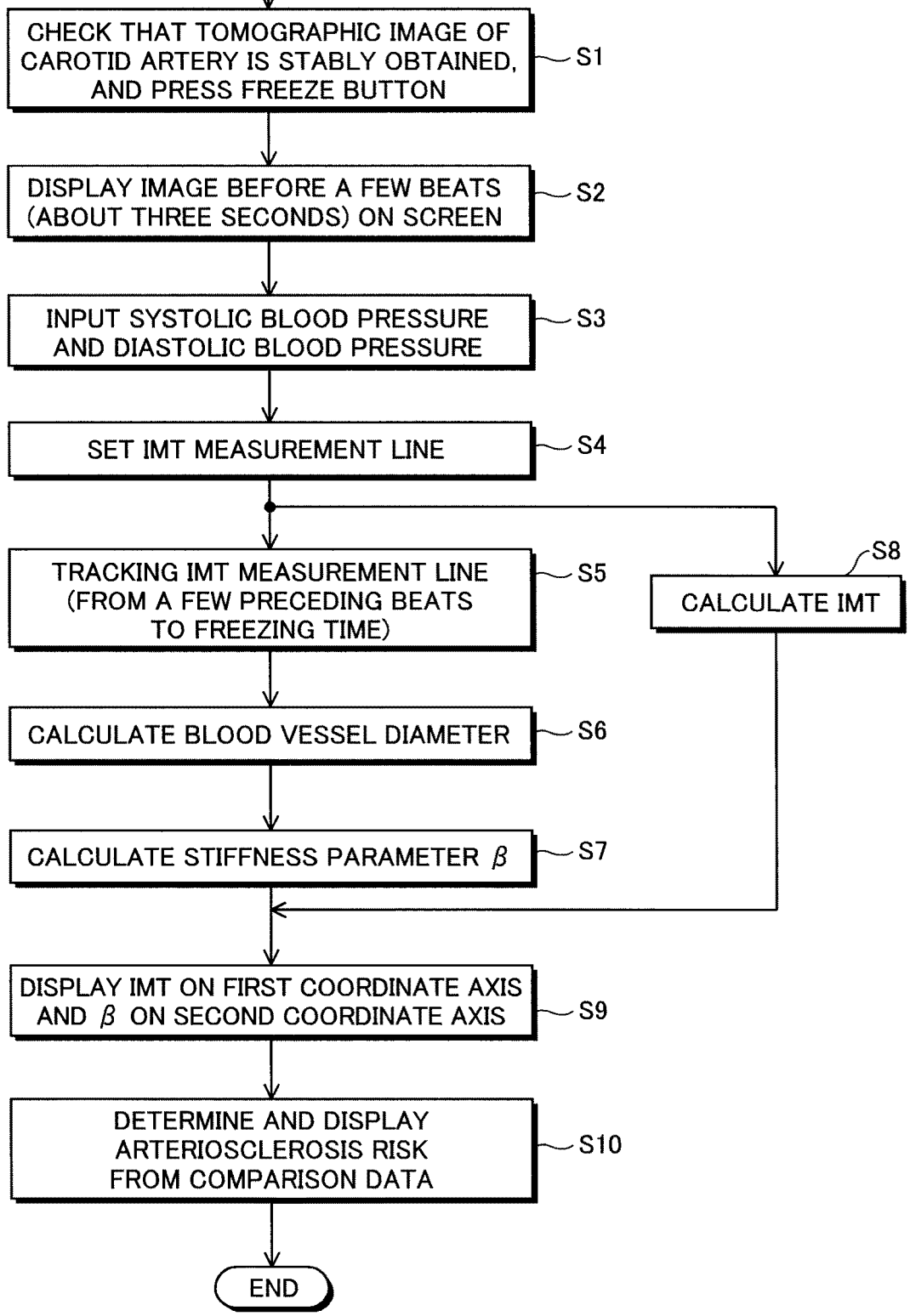
FIG. 2 is a flowchart showing the procedure of a measuring method according to the first embodiment of the present invention.
Figure 3:
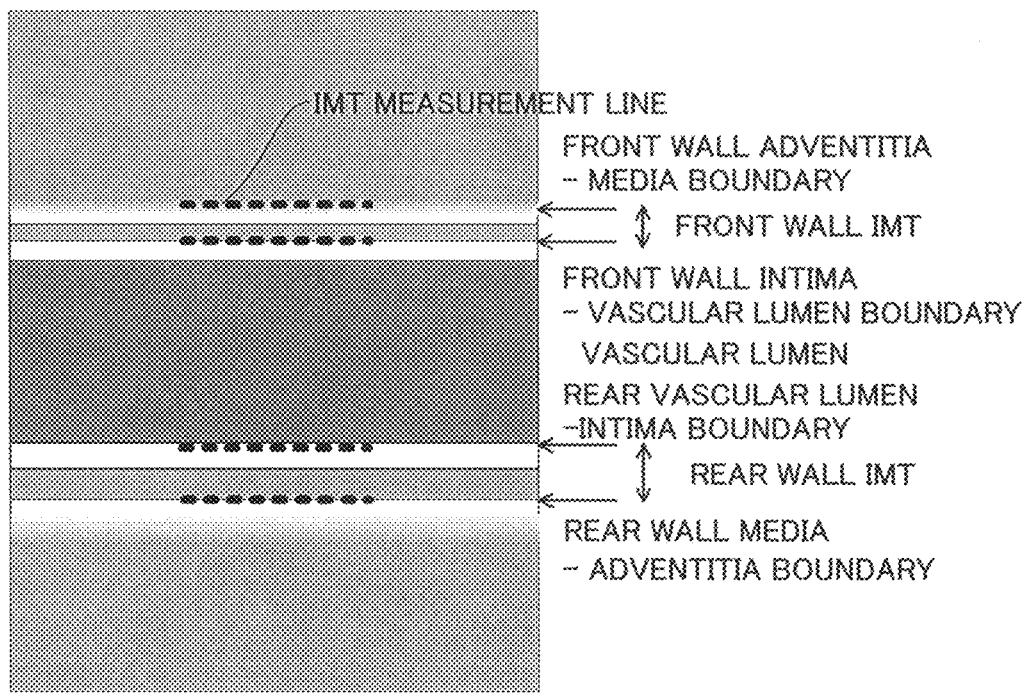
FIG. 3 is a conceptual diagram showing conditions in which an IMT measurement line is set from an ultrasonic image.
Figure 4:
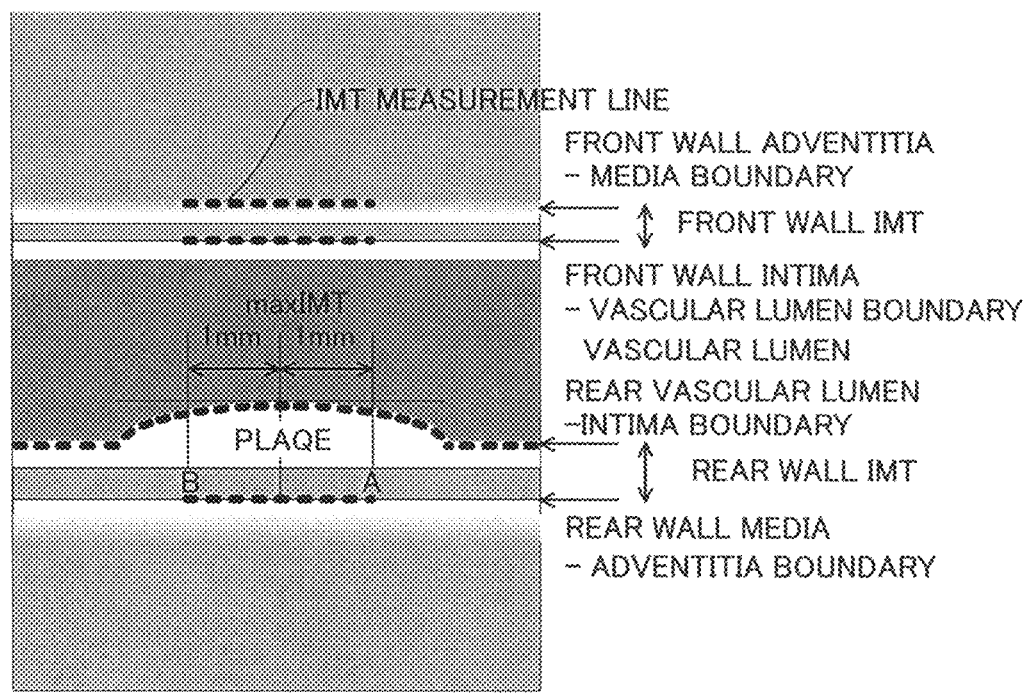
FIG. 4 is a conceptual diagram showing conditions in which the IMT measurement line is set when there is plaque in the ultrasonic image.
Figure 5:
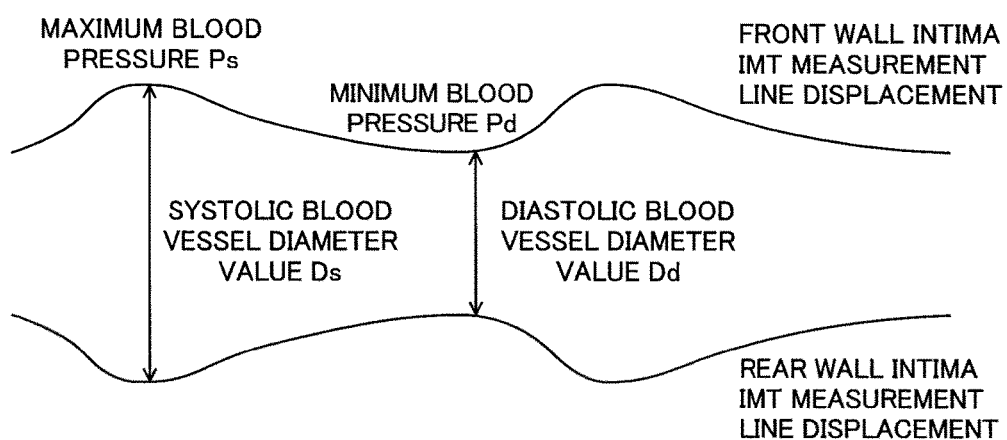
FIG. 5 is a line diagram showing, through tracking, a state in which a blood vessel wall is changed.
Figure 6:
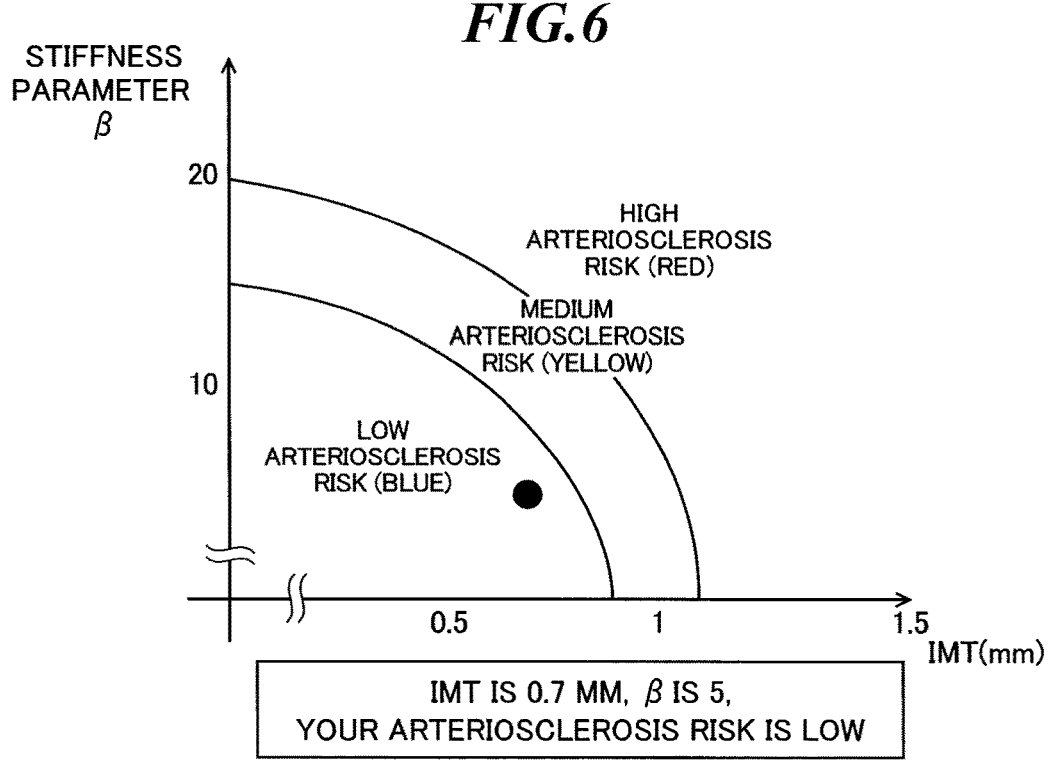
FIG. 6 is a diagram showing a display screen displaying IMT-β combination coordinates in two-dimensional coordinates in which the degree of arteriosclerosis risk is displayed on a zone basis.
Figure 7:
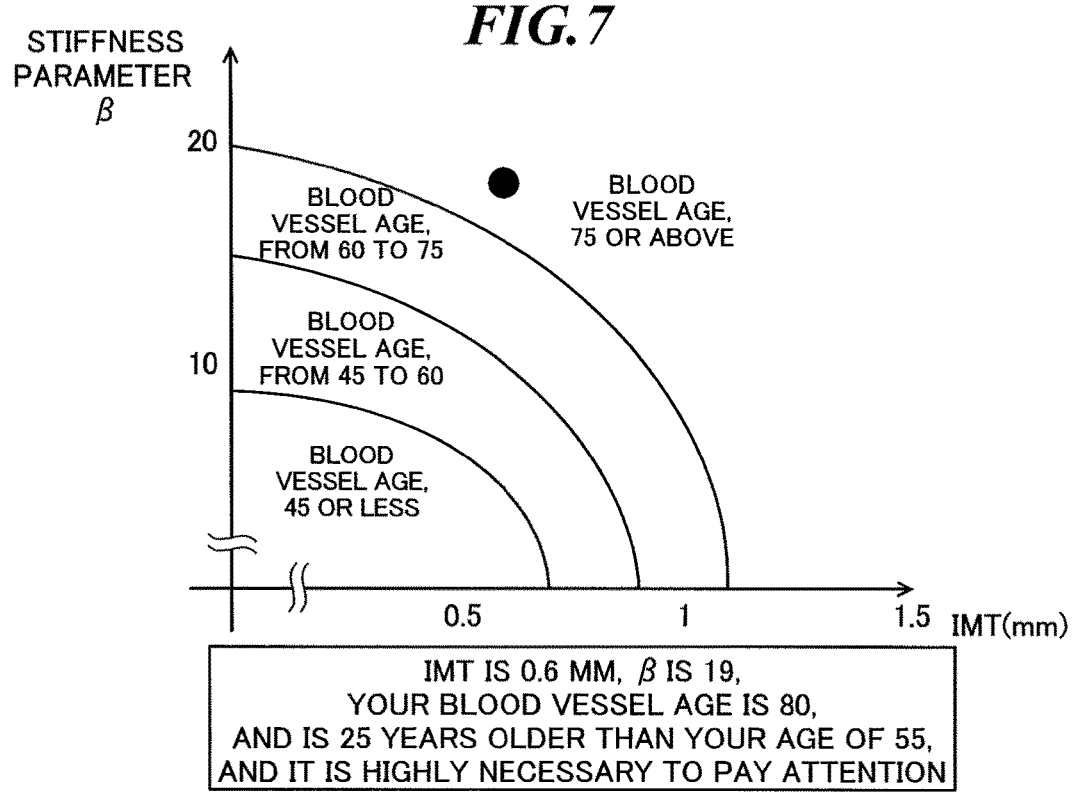
FIG. 7 is a diagram showing a display screen displaying IMT-β combination coordinates in two-dimensional coordinates in which the age of a blood vessel is displayed on a zone basis.

FIG. 1 is a block diagram showing the configuration of an ultrasonic diagnostic device according to a first embodiment of the present invention; FIG. 2 is a flowchart showing the procedure of a measuring method; FIGS. 3 and 4 are conceptual diagrams showing conditions in which the boundary lines of vascular membranes are set; FIG. 5 is a line diagram showing a state in which a blood vessel wall is changed; and FIGS. 6 and 7 show examples of a display screen.

The ultrasonic diagnostic device according to the first embodiment includes an ultrasonic probe for transmitting and receiving ultrasound and an ultrasonic diagnostic device main body. The ultrasonic diagnostic device main body has the functions of: controlling the transmitting and receiving of ultrasound; generating, based on an acquired reception signal, image data representing an ultrasonic image; measuring elastic indices indicating the intima media thickness (IMT) of a blood vessel and the dynamic characteristic of the blood vessel; and displaying the IMT and the elastic indices on a display. The ultrasonic diagnostic device main body has the function of storing arteriosclerosis risk comparison information serving as materials utilized for diagnosis and is provided with the display for displaying the diagnosis result and a blood pressure meter for measuring blood pressure.

The ultrasonic probe 101 is a probe of convex type, linear scan type, sector scan type or the like, which is used to be pressed onto a body under test. The ultrasonic probe 101 is provided with a plurality of ultrasonic transducers that constitute a one-dimensional or two-dimensional transducer array. These ultrasonic transducers transmit, based on a drive signal that is applied, ultrasound to the body under test, and receive ultrasonic echo reflected off the body under test to output a reception signal.

Each ultrasonic transducer is formed with a vibrator in which electrodes are formed on both ends of a material having piezoelectricity (a piezoelectric member) such as a piezoelectric ceramic like PZT (Pb (lead) zirconate titanate) and a polymeric piezoelectric element like PVDF (polyvinylidene difluoride). When a voltage in the form of pulses or a continuous wave is applied to the electrodes of the vibrator, the piezoelectric member expands and contracts. With this expansion and contraction, ultrasound waves in the form of pulses or a continuous wave is generated from each vibrator, and these ultrasound waves are combined to form an ultrasonic beam. Each vibrator receives traveling ultrasound waves to expand and contract, and thus generates electrical signals. These electrical signals are output as the reception signals of the ultrasound waves.

The ultrasonic diagnostic device main body is provided with a transmit/receive control portion 111, a transmission circuit 113, a reception circuit 115, a tomographic image formation portion 117, a display processing portion 119, an IMT measurement line setting portion 121, an IMT calculation portion 123, a measurement tracking portion 125, a blood vessel wall displacement calculation portion 127, a blood pressure measurement portion 129, a l calculation portion 131 and an arteriosclerosis risk determination portion 133.

As peripheral devices of the ultrasonic diagnostic device main body, a blood pressure meter 103 and a display 105 are provided; the blood pressure measurement portion 129 receives the measurement result from the blood pressure meter 103, and the display processing portion 119 controls the display of the display 105. Arteriosclerosis risk comparison information 107 used in the arteriosclerosis risk determination portion 133 can also be supplied from a storage device provided in the ultrasonic diagnostic device main body.

The transmit/receive control portion 111 sequentially sets, through the transmission circuit 113 and the reception circuit 115, a direction in which the ultrasonic beam of the ultrasonic probe 101 is transmitted and a direction in which the ultrasonic echo is received; the transmit/receive control portion 111 has the transmission control function of selecting a transmission delay pattern according to the set transmission direction, and the reception control function of selecting a reception delay pattern according to the set reception direction.

Here, the transmission delay pattern is a pattern of a delay time given to a drive signal of each ultrasonic transducer so that the ultrasonic beam is generated in a desired direction by ultrasound transmitted from a plurality of ultrasonic transducers; the reception delay pattern is a pattern of a delay time given to a reception signal so that the ultrasonic echo is extracted from a desired direction through ultrasound received by a plurality of ultrasonic transducers. A plurality of transmission delay patterns and a plurality of reception delay patterns are stored in a storage device, and are selected and utilized according to the situation.

The transmission circuit 113 has a plurality of channels, and generates a plurality of drive signals that are applied to a plurality of ultrasonic transducers, respectively. Here, based on the reception delay pattern selected by the transmit/receive control portion 111, delay time corresponding to each of the drive signals can be individually given to a plurality of drive signals. The transmission circuit 113 may adjust the amount of delay of a plurality of drive signals to supply them to the ultrasonic probe 101 such that ultrasound transmitted from a plurality of ultrasonic transducers forms an ultrasonic beam; the transmission circuit 113 may supply to the ultrasonic probe 101 a plurality of drive signals that are formed such that ultrasound simultaneously transmitted from a plurality of ultrasonic transducers reaches the entire image sensing region of a body under test.

The reception circuit 115 has a plurality of channels, and receives a plurality of analogue reception signals output from a plurality of ultrasonic transducers, amplifies them, and converts them into digital reception signals. Moreover, based on the reception delay pattern selected by the transmit/receive control portion 111, the reception circuit 115 gives delay time corresponding to each of the reception signals to a plurality of reception signals, and adds together the reception signals to perform reception focus processing. Performing this reception focus processing forms sound ray signals (sound ray data) in which the focus of ultrasonic echo is narrowed.

Then, the sound ray data is subjected to envelope detection processing through low-pass filter processing or the like, and is corrected for attenuation due to distance by STC (sensitivity time gain control) according to the depth of a location where ultrasound is reflected.

The sound ray data on which the processing is performed in this way is sequentially stored in a cine memory having a memory capacity for storing sound ray data corresponding to a plurality of frames. The reception circuit 115 has the function of generating image data, and, in a live mode, inputs sound ray data that is directly supplied, and, in a freeze mode, inputs the sound ray data that is supplied from the cine memory. Then, the reception circuit 115 performs preprocess processing such as log(logarithmic) compression or gain adjustment on the input sound ray data to generate image data, and outputs it to the tomographic image formation portion 117 or the IMT measurement line setting portion 121.

The tomographic image formation portion 117 converts (raster conversion) the image data on the ultrasonic image supplied from the reception circuit 115 into image data corresponding to the scanning method of normal television signals, then performs necessary image processing such as gradation processing and transmits it to the display processing portion 119.

On the other hand, the IMT measurement line setting portion 121 sets a ROI (region of interest) on the ultrasonic image displayed by the image data supplied from the reception circuit 115, sequentially selects, in the depth direction of the ROI, a predetermined number of lines (sound rays) that can be determined to be an IMT boundary position and extracts image data in the selected lines. FIG. 3 is a conceptual diagram showing that the boundary between an adventitia and a media in a blood vessel front wall, the boundary between an intima and a vascular lumen, the boundary between a vascular lumen and an intima in a blood vessel rear wall and the boundary between the media and the adventitia are selected from the ultrasonic image and are set at the IMT measurement lines. FIG. 4 is a conceptual diagram showing a case in which a state where plaque is formed inside the rear wall is detected. FIG. 4 shows that the boundary between a rear wall vascular lumen and an intima partially extends toward the vascular lumen.

When the IMT measurement line setting portion 121 supplies the image data extracted with respect to the selected lines to the IMT calculation portion 123, the IMT calculation portion 123 automatically measures the IMT of a blood vessel after verifying the reliability of the image data. Thus, the IMT calculation portion 123 performs image processing such as noise suppression processing using a low-pass filter or a median filter on the extracted image data to generate reference data. The reference data generated from the image data is made to correspond to patient information or inspection information or the age, the sex or the like of the patient, and is stored in a predetermined storage device. Typical reference data may be previously stored according to the age, the sex or the like of the patient.

Then, according to the operation of the operator or the procedure of the automatic operation of the device, the reference data stored in the storage device or the reference data generated from the extracted image data is selected as reference data that is actually used. Within the ROI (region of interest) set with respect to the image, an evaluation region (a region in the depth direction) in which the reliability of the IMT measurement is evaluated is set, and, in the set evaluation region, the reliability of the IMT measurement is calculated. For example, in the set evaluation region, the positions of the image data and the reference data in the depth direction are made coincide with each other, and thereafter, with respect to the predetermined number of lines in the depth direction in the set region, the absolute value of the difference between the image data and the reference data is integrated, or the distribution value of the difference is determined, with the result that the reliability of the IMT measurement can be calculated. Then, the calculated value of the reliability of the IMT measurement is compared with a threshold, and thus the reliability of the IMT measurement is determined.

When the reliability of the IMT measurement in the set evaluation region is satisfactory, the IMT calculation portion 123 automatically measures the IMT of a blood vessel with the image data obtained in the selected lines within the evaluation region. In a carotid artery ultrasonic inspection, the diameter of a blood vessel and a max (maximum) IMT are measured, and, furthermore, in order for an accurate size determination to be made as to the deposition of plaque and the like, a mean (average) IMT is calculated. This mean IMT is calculated by determining, for example, the max IMT and IMTs at positions A and B one centimeter away from both ends thereof and calculating the average [max IMT+IMT (A)+IMT (B)]/3 of the three points. The IMT thus determined is transmitted to the arteriosclerosis risk determination portion 133.

The IMT measurement lines that are set by the IMT measurement line setting portion 121 and that are highly reliable for the IMT measurement can be employed as reference lines that are used, at the measurement tracking portion 125, for automatically tracking a blood vessel wall displacement waveform and the diameter of a blood vessel. In the measurement line tracking portion 125, the specific point of the set IMT measurement line is determined to be a subject to be tracked, image processing is performed on the image data and the lines are automatically identified and tracked, with the result that variations in the position of a blood vessel wall are tracked. As the method of tracking the measurement line, there are various methods such as a tomographic image pattern matching method, a zero cross point method, a tissue Doppler method and a phase difference tracking method, and it is needless to say that any method may be employed.

Since, in the image data, a vascular lumen generally has a low signal level, and this results in the failure of tracking, the IMT measurement line that is shifted substantially in parallel toward an adventitia may be determined to be the subject to be tracked. As described above, based on the IMT measurement line, the starting line for the tracking is set, and thus it is possible to decrease the measurement period and remove load imposed on a doctor or the like and a person to be tested.

Moreover, by drawing s line between its position when a blood vessel contracts and its position when it expands, it is possible to measure Dd/Ds. The blood vessel wall displacement calculation portion 127 calculates, based on the blood vessel wall displacement waveform, the heart systolic blood vessel diameter Ds and the heart diastolic blood vessel diameter Dd.

FIG. 5 shows the change of a blood vessel wall along the time axis. The blood vessel diameter D becomes the maximum value Ds at the heart systolic; it becomes the minimum value Dd at the heart diastolic stage. The blood vessel wall displacement calculation portion 127 tracks, from the image data, the change of blood vessel diameter D to determine the maximum blood vessel diameter value Ds and the minimum blood vessel diameter value Dd, and transmits them to the β calculation portion 131.

On the other hand, since blood pressure P that is measured with the cuff-type blood pressure meter 103 becomes the maximum value Ps and the minimum value Pd according to the contraction and the expansion of a hear, it is possible to easily read the blood pressure P from the maximum value and the minimum value of a blood pressure indication value. Such blood pressure data is automatically or manually input to the blood pressure measurement portion 129 and is furthermore transmitted to the β calculation portion 131.

The β calculation portion 131 calculates the stiffness parameter β from $\beta=[\text{Log}(Ps/Pd)]/(Ds/Dd-1)$, and transmits it to the arteriosclerosis risk determination portion 133.

The arteriosclerosis risk determination portion 133 takes into consideration the input stiffness parameter β and the IMT supplied from the IMT calculation portion 123 in a composite manner to determine arteriosclerosis risk. Here, a method can be employed of recognizing the arteriosclerosis risk by using the following procedure: as shown in FIG. 6, a two-dimensional coordinate system where the first coordinate axis represents the IMT and the second coordinate axis represents the stiffness parameter β is prepared, regions where the degree of the arteriosclerosis risk is classified into high, medium and low degrees are drawn on the IMT-β plane, and the state of the blood vessel of a patient is displayed on the IMT-β plane.

The arteriosclerosis risk determined by evaluating the results obtained by measuring a large number of persons to be tested is stored, as the arteriosclerosis risk comparison information 107, in a storage device, and is read out and utilized from the storage device when the arteriosclerosis risk determination portion 133 makes a determination.

As shown in FIG. 7, the arteriosclerosis risk comparison information 107 may be that in which regions classified according to the age of a blood vessel are set. The age of a blood vessel is determined by employing an average index value for an age group from the results obtained by performing measurements on a large number of persons to be tested. Alternatively, it is possible to comply with an index value in a boundary where a person to be tested can be determined to be a healthy person.

The formed graph in the two-dimensional coordinate system is supplied to the display processing portion 119.

The display processing portion 119 generates image data for display based on the image data supplied from the tomographic image formation portion 117 and the graph in the two-dimensional coordinate system input from the arteriosclerosis risk determination portion 133. The display processing portion 119 may additionally have the function of performing image processing such as linear gradation processing including gain adjustment and contrast adjustment and non-linear gradation processing including γ correction. A D/A converter is further provided, and thus the image data for display is converted into analog image signals, which are output to the display 105. The display 105, for example, is a raster-scan type LCD display, and displays, based on the image signals resulting from the analog conversion by the display processing portion 119, moving images or a still image of an ultrasonic image, the graph in the two-dimensional coordinate system where the IMT and β are plotted or the like.

It is possible for a doctor or a person to be tested to intuitively and accurately recognize the risk for developing arteriosclerosis from the composite state of morphological information (IMT) of a blood vessel and elastic indices (stiffness parameter β) in the two-dimensional coordinate graph displayed on the display 105.

The operation of the ultrasonic diagnostic device according to the first embodiment of the present invention will now be described with reference to the flowchart shown in FIG. 2.

First, in step S1, it is found that moving images of a carotid artery tomographic image displayed on the display 105 are stably acquired, and then a freeze button is pressed. Thus, moving images that have been acquired since about a few beats before the pressing of the freeze button (about three seconds) up to now are stored in a memory, and the frame that was first stored is displayed on the screen of the display 105 (step S2).

The maximum blood pressure obtained with the cuff-type blood pressure meter is considered to be the contracting period blood pressure Ps and the minimum blood pressure is considered to be the expanding period blood pressure Pd; they are input manually or online (step S3).

As shown in FIG. 3, the IMT measurement line setting portion 121 sets the IMT measurement lines in the tomographic image (step S4). The measurement tracking portion 125 uses the images acquired since the first image is acquired until the freeze button was pressed to track the IMT measurement lines (step S5), with the result that the blood vessel wall displacement waveform shown in FIG. 5 is determined. The blood vessel wall displacement calculation portion 127 calculates, from this blood vessel wall displacement waveform, the heart systolic blood vessel diameter Ds and the heart diastolic blood vessel diameter Dd (step S6).

In step S7, the β calculation portion 131 uses the following equation $\beta=[Log(Ps/Pd)]/(Ds/Dd-1)$ to calculate the stiffness parameter β. The value of β is preferably the average value on sound ray lines where the IMT measurement lines are drawn; even if, due to restrictions such as calculation time, the value of β is one specific sound ray line, a significant effect is not encountered.

On the other hand, the IMT calculation portion 123 receives the image data obtained in the IMT measurement lines set in step S4 to automatically measure the IMT of a blood vessel (step S8). In order for an accurate size determination to be made as to the deposition of plaque and the like, for example, the mean IMT is utilized that is obtained by calculating the average [max IMT+IMT (A)+IMT (B)]/3 of three points, namely, the max IMT and IMTs at positions A and B one centimeter away from both ends thereof.

The IMT thus determined and the stiffness parameter β determined in the β calculation portion 131 are plotted with respect to the first coordinate axis and the second coordinate axis, respectively, with the result that they are displayed two-dimensionally (step S9).

Finally, in step 10, the arteriosclerosis risk determination portion 133 compares the combination of the IMT and the β with the arteriosclerosis risk comparison information 107 to evaluate the arteriosclerosis risk of the blood vessel of the person to be tested. The evaluation result is displayed, on the display 105, in the form of, for example, the graph shown in FIG. 6. In the example shown in FIG. 6, since, in the two-dimensional coordinate system where the IMT of a carotid artery with respect to the body under test and the stiffness parameter β serving as an elastic index of a blood vessel are represented by the level of the risk of developing arteriosclerosis on a region-by-region basis, the IMT and the elastic index of a blood vessel are combined and displayed as two-dimensional coordinates, it is possible to determine the risk of developing arteriosclerosis more accurately than the diagnosis of the IME alone or the diagnosis of the β alone, and this allows the risk to be conveyed in a more understandable manner to the doctor or the person to be tested.

The graph of FIG. 6 is preferably formed such that the development risk of the person to be tested is simply understood, by using the following procedure: for example, in a two-dimensional coordinate plane where the risk of developing the arteriosclerosis is classified into high, medium and low ranks, and where the regions representing the ranks are individually represented by different colors such as red, yellow and blue, the coordinates represented by the IMT of the person to be tested and the β are plotted. Generally, even when the IMT is large, if the elastic index is small, the arteriosclerosis risk is low; even when the elastic index is large, if the IMT is small, the arteriosclerosis risk is also low. Thus, risk classification zones are displayed circularly around the origin.

That the arteriosclerosis risk is represented by the age of a blood vessel is effective for the recognition of the development risk to be enhanced. FIG. 7 shows that the average IMT and β for the age is calculated from the data of IMTS and β on a large number of persons to be tested, and that they are represented by individual age groups on a region-by-region basis. The coordinates represented by the IMT and β of the person to be tested are plotted, and thus the age of a blood vessel is found, and, for example, in the margin of the graph of FIG. 7, a comment is displayed that says "Your blood vessel is 80 years old. Your blood vessel age is 25 years older than your age of 55, and it is highly necessary to pay attention on it", with the result that it is possible to call attention to the risk by comparing it with the actual age.

Second Embodiment

A second embodiment of the present invention will now be described. Although, in the first embodiment, the stiffness parameter β is used as the elastic index, the same holds true even if variations in blood vessel diameter, an elastic modulus and a WI (wave intensity) are used. In the second embodiment, an elastic modulus is used as the elastic index of a blood vessel.

Figure 8:
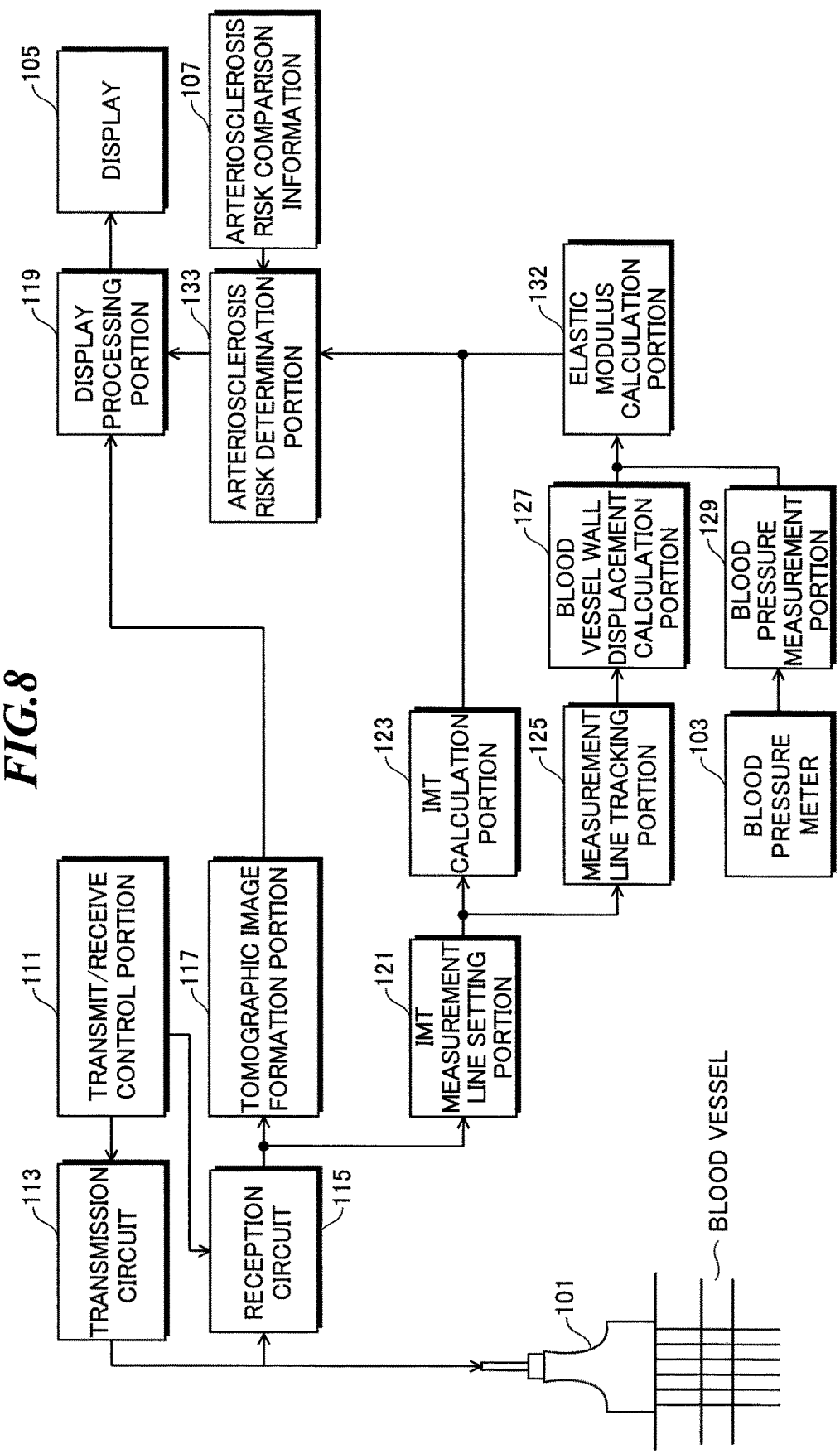
FIG. 8 is a block diagram showing the configuration of an ultrasonic diagnostic device according to a second embodiment of the present invention.

FIG. 8 is a block diagram showing the configuration of an ultrasonic diagnostic device according to the second embodiment. Since FIG. 8 differs from FIG. 1 only in that the β calculation portion 131 is replaced with an elastic modulus calculation portion 132, like components are identified with the same reference numerals as the first embodiment, and their description will not be repeated.

In the case of the second embodiment using an elastic modulus as the elastic index of a blood vessel, the measurement line tracking portion 125 also tracks IMT measurement lines in the front wall and the boundary between the rear wall adventitia and the media to determine the maximum value Td and the minimum value Ts of the IMT in one beat, and the elastic modulus E is determined from the following equation $E=(Ps-Pd)/[(Td-Ts)/Td]$. In this case, since the measurement location of the elastic modulus E is automatically restricted to be within the IMT, the stable elastic modulus data is obtained without being dependent on the measurement location, with the result that, advantageously, the elastic modulus data is easily compared with other measurement data.

When a more advanced algorism is used, the media IMT measurement line and the adventitia-media boundary IMT measurement line are divided, and the elastic modulus of each region may be measured.

As described above, the operation of the measurement processing portion shown in FIG. 8 differs from that in the first embodiment, but other respects are the same as the first embodiment.

In an embodiment using the WI (wave intensity) as the elastic index of a blood vessel, it is preferable to replace the elastic modulus calculation unit with a WI calculation unit to calculate the product of the derivative value of the blood pressure P with respect to time and the derivative value of a blood flow rate U with respect to time. As the blood flow rate U, the value of a carotid artery can be determined with a Doppler measurement unit using an ultrasonic probe.

In an embodiment using variations in blood vessel diameter as the elastic index of a blood vessel, if the procedure with respect to the blood pressure meter is removed, the same method described above can be used. It is possible to obtain variations in blood vessel diameter from the ultrasonic image of a blood vessel.

Although, in the above-described embodiments, the transmit/receive control portion 111, the tomographic image formation portion 117, the display processing portion 119, the IMT measurement line setting portion 121, the IMT calculation portion 123, the measurement line tracking portion 125, the blood vessel wall displacement calculation portion 127, the blood pressure measurement portion 129, the β calculation portion 131, the elastic modulus calculation portion 132, the arteriosclerosis risk determination portion 133 and the like are formed with a central processing unit (CPU) and software for making the CPU perform various types of processing, they may be formed with a digital circuit or an analog circuit. The software is stored in a storage portion (not shown).

Third Embodiment

Like components are identified with like reference numerals, and their description will not be repeated.

Figure 9:
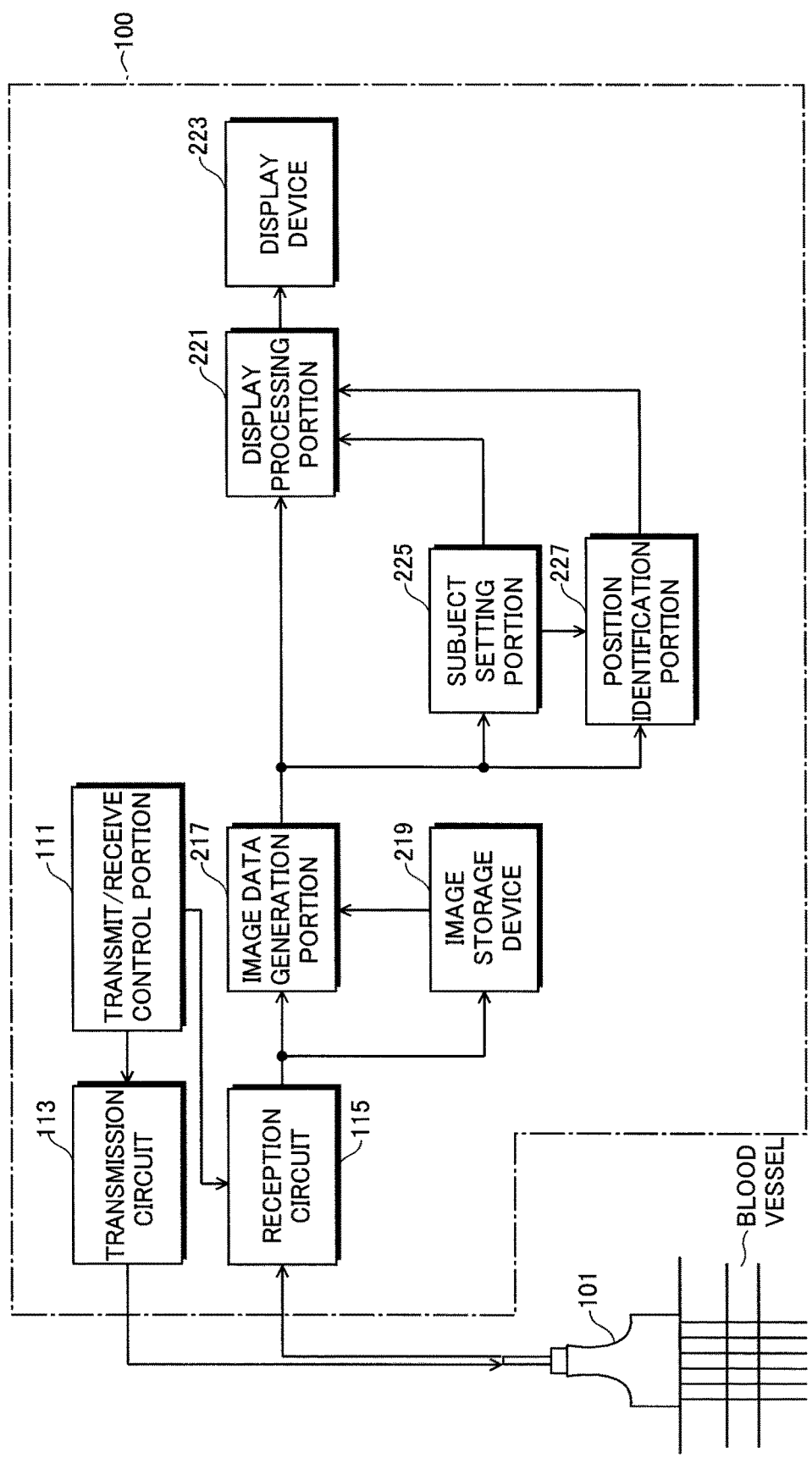
FIG. 9 is a block diagram showing the configuration of an ultrasonic diagnostic device according to a third embodiment of the present invention.

FIG. 9 is a block diagram showing a configuration of an ultrasonic diagnostic device according to a third embodiment of the present invention, and the same parts as in FIG. 1 are identified with the same symbols, and their description will not be repeated.

As shown in FIG. 9, the ultrasonic diagnostic device according to this embodiment includes the ultrasonic diagnostic device main body 100 and the ultrasonic probe 101.

The ultrasonic transducer of the ultrasonic probe 101 transmits, based on a drive signal that is applied, ultrasound to the body under test such as a carotid artery blood vessel 300, receives ultrasonic echo reflected off the body under test and outputs an ultrasonic image signal along a measurement line set to the body under test.

The ultrasonic diagnostic device main body 100 includes: the transmit/receive control portion 111 that controls the transmitting and receiving of ultrasound; the transmission circuit 113; the reception circuit 115; an image data generation portion 217 that generates, based on the ultrasonic image signal output from the ultrasonic probe 101, image data representing the ultrasonic image of the body under test along the measurement line; an image storage device 219 that temporarily records a plurality of sheets of generated image data; a display processing portion 221 that generates a graph obtained by plotting, in a three-dimensional coordinate system, the plurality of sheets of image data input from the image storage device 219; and a display device 223 that displays the generated graph.

The ultrasonic diagnostic device main body 100 is further provided with: a subject setting portion 225 that sets a subject region to be measured in the ultrasonic image represented by the generated image data; a position identification portion 227 that calculates, while tracking, from the ultrasonic image, the measurement position in the subject region to be measured over a plurality of ultrasonic images, a length in a vertical direction with respect to the measurement position; and the display processing portion 221 that displays the temporal change of the subject to be measured in a three-dimensional coordinate system where the position of the subject region to be measured is displayed on the first axis, a length measured in a vertical direction with respect to the position is displayed on the second axis and time is displayed on the third axis.

In a storage device provided in the transmit/receive control portion 111, a plurality of transmission delay patterns and a plurality of reception delay patterns are stored, and they are selected and utilized according to the situation.

The transmission circuit 113 has a plurality of channels, and generates a plurality of drive signals that are applied to a plurality of ultrasonic transducers, respectively.

The reception circuit 115 has a plurality of channels, and receives a plurality of analogue reception signals output from a plurality of ultrasonic transducers, amplifies them, and converts them into digital reception signals.

Then, the sound ray data is subjected to envelope detection processing, and is thereafter corrected for attenuation due to distance by STC (sensitivity time gain control) according to the depth of a location where ultrasound is reflected.

The sound ray data on which the processing is performed in this way is sequentially stored in the image storage device 219 having a memory capacity for storing sound ray data equivalent to a plurality of frames on a frame-by-frame basis. The image data generation portion 217, in a live mode, inputs sound ray data that is directly supplied, and, in a freeze mode, inputs the sound ray data that is supplied from the image storage device 219, and performs preprocess processing such as log (logarithmic) compression or gain adjustment on the input sound ray data to generate image data, and outputs it to the subject setting portion 225. The subject setting portion 225 sets, based on the image data input from the image data generation portion 217, the subject region to be measured in the ultrasonic image.

Figure 10:
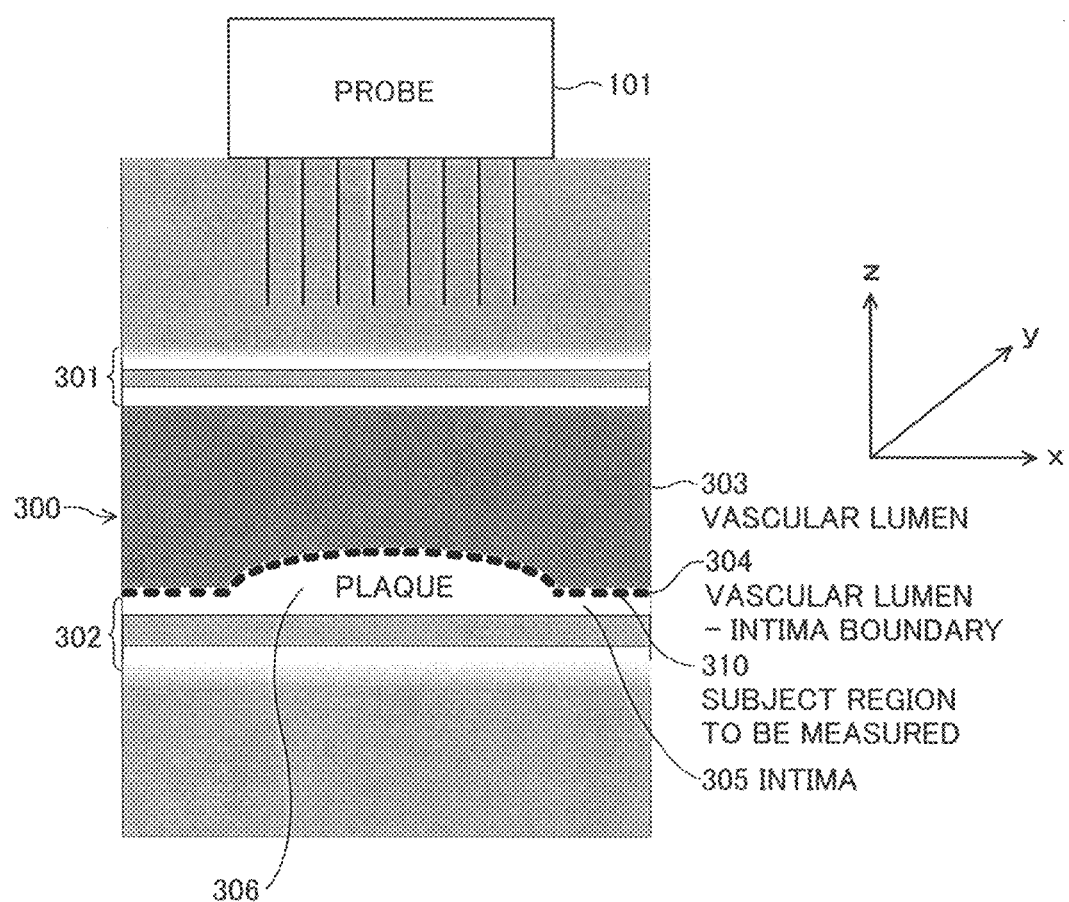
FIG. 10 is an ultrasonic image diagram showing the concept of setting a subject region to be measured in the third embodiment of the present invention.

FIG. 10 shows the concept of setting the subject region to be measured based on the image data. The transducer array of the ultrasonic probe 101 is placed such that the measurement line coincides with a flow direction on the blood vessel 300 of a carotid artery. The measurement signals obtained from the ultrasonic probe 101 cover the blood vessel walls of the front wall 301 and the rear wall 302 in the blood vessel 300, and display an ultrasonic tomographic image. When, as the subject region to be measured 310, the boundary 304 of the vascular lumen 303 and the intima 305 of the rear wall 302 are specified, the subject setting portion 225 determines, based on the image data, the position of the subject region to be measured 310 in the ultrasonic image.

As the method of determining the position of the subject region to be measured 310, there are various methods such as a tomographic image pattern matching method, a zero cross point method, a tissue Doppler method and a phase difference tracking method; it is needless to say that any method may be used. Although, in FIG. 10, the subject region to be measured 310 is deformed by the plaque 306, the subject setting portion 225 accurately follows the deformation of the vascular lumen-intima boundary 304 to determine the position of the subject region to be measured 310.

Referring back to FIG. 9, the position identification portion 227 tracks, with respect to each of a plurality of measurement points in the subject region to be measured 310, the corresponding point over a plurality of tomographic images, and calculates its depth. The calculation result is supplied to the display processing portion 221. The tracking of the measurement position of the set subject region to be measured 310 over time can be performed with the brightness information and the phase information. The tracking is preferably performed with a common method such as a pattern matching using a correlation function. When the subject region to be measured 310 is the vascular lumen-intima boundary 304, since the brightness difference is large, it is possible to achieve an automatic detection even by performing appropriate threshold processing using a brightness value.

The display processing portion 221 prepares a three-dimensional coordinate system in which the position of the subject region to be measured is displayed on the first axis, the distance measured in a vertical direction with respect to the position is displayed on the second axis and time is displayed on the third axis, and plots, on the three-dimensional coordinate system having the time axis as one axis, the position of the subject region to be measured and the depth of the subject region to be measured, with the result that a graph using equal time lines is formed. This graph is supplied to the display device 223 as graph data for display on the display device 223.

Figure 11:
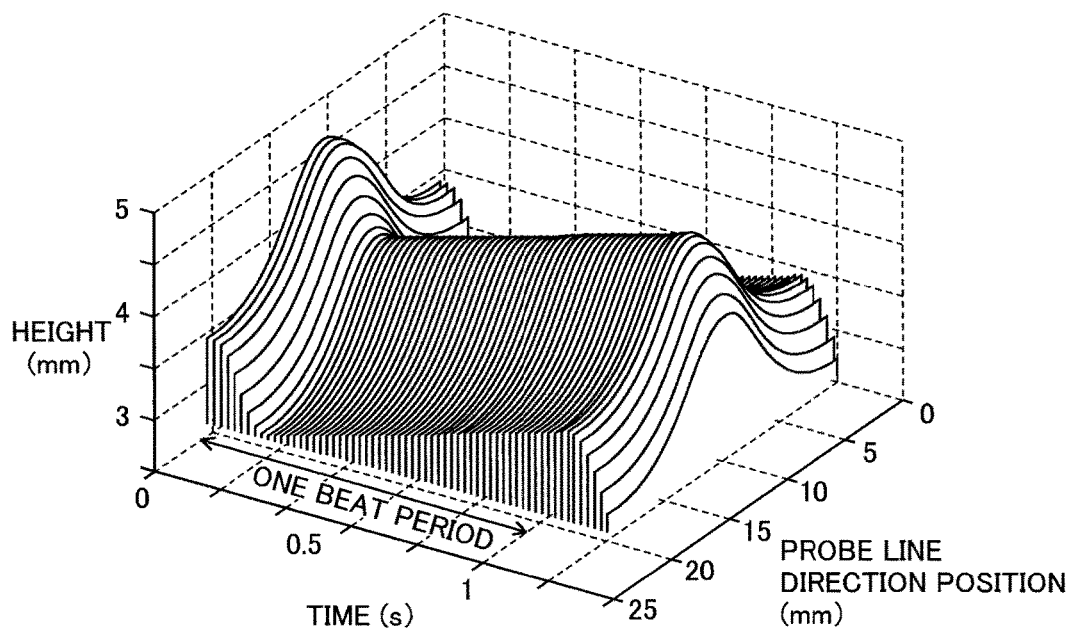
FIG. 11 is a diagram showing an example of a display of a measurement result by the ultrasonic diagnostic device according to the third embodiment of the present invention.

The display device 223 displays a three-dimensional graph as shown in, for example, FIG. 11, according to the input graph data on a display.

Although, as described above, the transmit/receive control portion 111, the image data generation portion 217, the display processing portion 221, the subject setting portion 225, the position identification portion 227 and the like are formed with the central processing unit (CPU) and software for making the CPU perform various types of processing, they may be formed with a digital circuit or an analog circuit. The software is stored in a storage portion (not shown).

In FIG. 11, with respect to the ultrasonic image of the rear wall vascular lumen-intima boundary 304 of a carotid artery that is acquired during one beat, a graph plotted in the three-dimensional coordinate system, in which the distance of a probe line direction where the transducers of the ultrasonic probe 101 are arranged is on the x-axis, the height of the subject region to be measured 310 is on the z-axis and time is on the y-axis, is cut along a simultaneous cross section perpendicular to the y-axis, thus profile lines are generated in regular intervals and the profile lines are displaced along the y-axis and are displayed in layers.

FIG. 11 shows a result obtained by performing a simulation on the hard, unbreakable, stable plaque 306. When the heart contracts to push out blood into an artery, then the blood pressure rises, the blood vessel rapidly expands and the height of the vascular lumen-intima boundary 304 is lowered, with the result that the blood vessel expands. Thereafter, since the heart gradually expands, the blood pressure gradually decreases, and the height is brought back to the original state, with the result that the blood vessel expands. The figure clearly shows the temporal change of the plaque portion; since the plaque 306 is hard, in the graph, almost no distortion is observed throughout one cardiac cycle.

Figure 12:
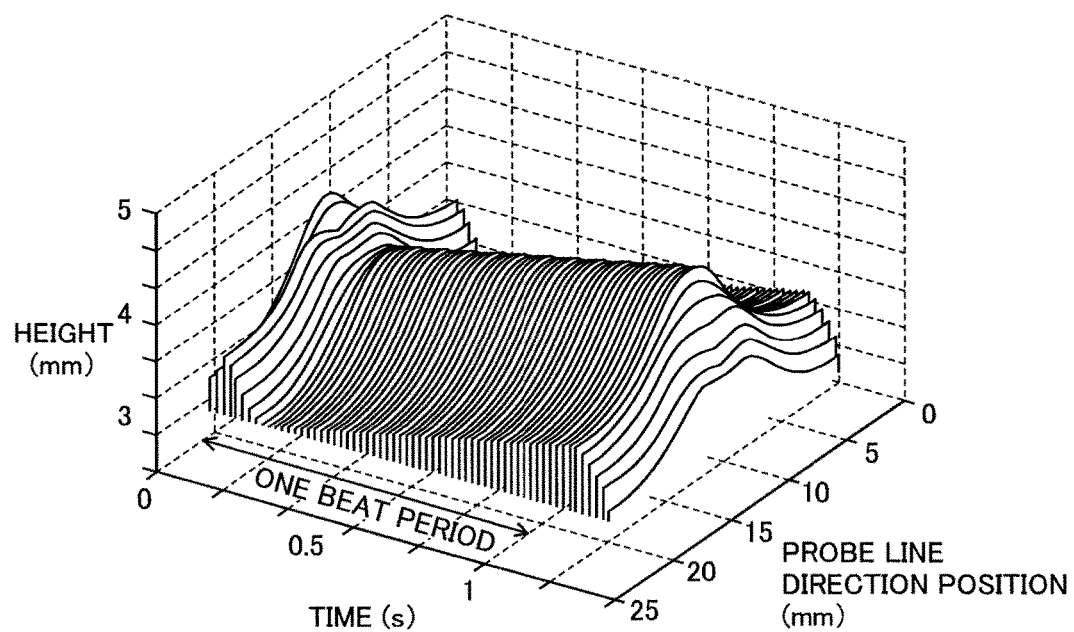
FIG. 12 is a diagram showing an example of a display of a measurement result of another subject by the ultrasonic diagnostic device according to the third embodiment of the present invention.

FIG. 12 is a graph showing a result obtained by performing, with the same display method as FIG. 11, a simulation on the soft, breakable, unstable plaque 306. The graph shows that, when the heart contracts and thus the blood vessel rapidly expands, the blood pressure rapidly increases and thus the soft portion of the plaque 306 in its middle is pushed to produce a recess.

FIGS. 11 and 12 are ones in which the surface shape of the vascular lumen-intima boundary 304 set in the subject region to be measured is cut along a simultaneous cross section, and the resulting profile lines are arranged in only one cardiac cycle in regular intervals in layers; since not only the shape of the expanded plaque 306 but also the irregularities of the profile lines are clearly observed, it is possible to visually understand even the property of the hardness of the plaque 306.

Figure 13:
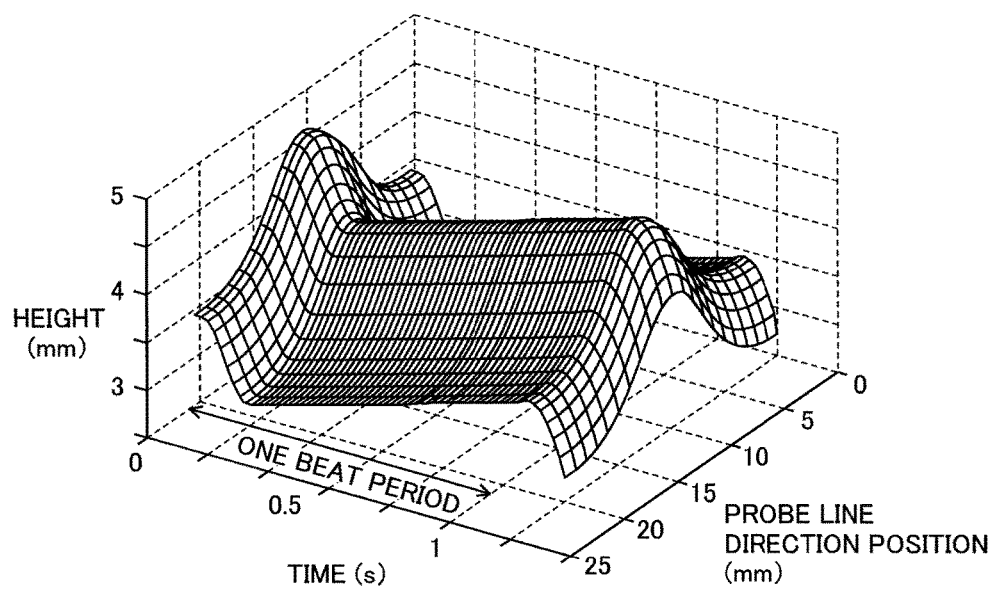
FIG. 13 is a diagram showing another display example by the ultrasonic diagnostic device according to the third embodiment of the present invention.
Figure 14:
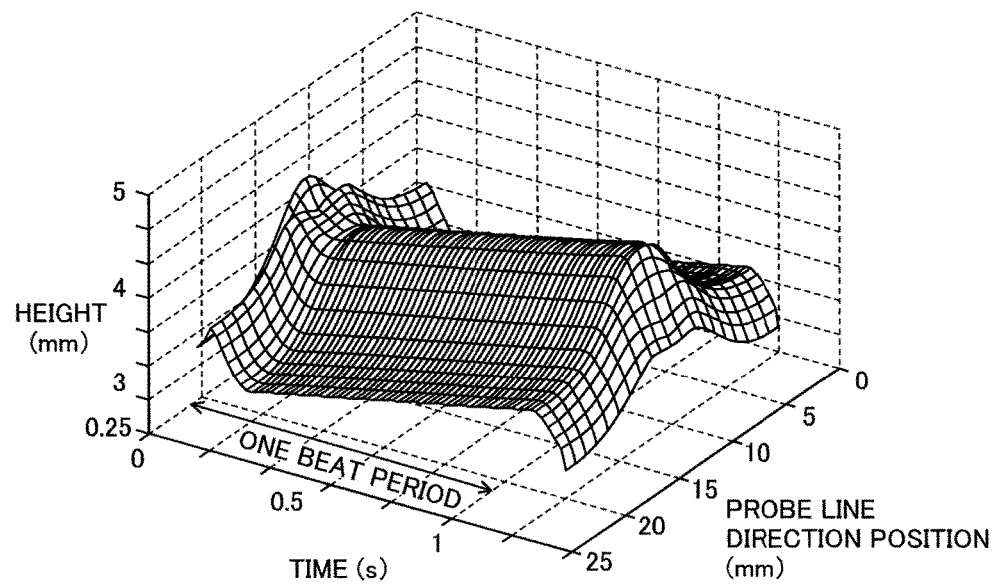
FIG. 14 is a diagram showing an example of a display of a measurement result of another subject with the display method of FIG. 13.

FIGS. 13 and 14 are graphs in which profile lines spaced regularly in the x-axis direction are added to the graphs displayed in FIGS. 11 and 12, and in which two types of profile lines are displayed in the form of a mesh. FIG. 13 shows a case where the hard plaque is used; FIG. 14 shows a case where the soft plaque is used. With this display method, it is possible to easily observe how the measurement position on the plaque varies with the pulse. As compared with FIGS. 11 and 12, it may be slightly difficult to observe variations in the shape of the entire plaque.

Figure 15:
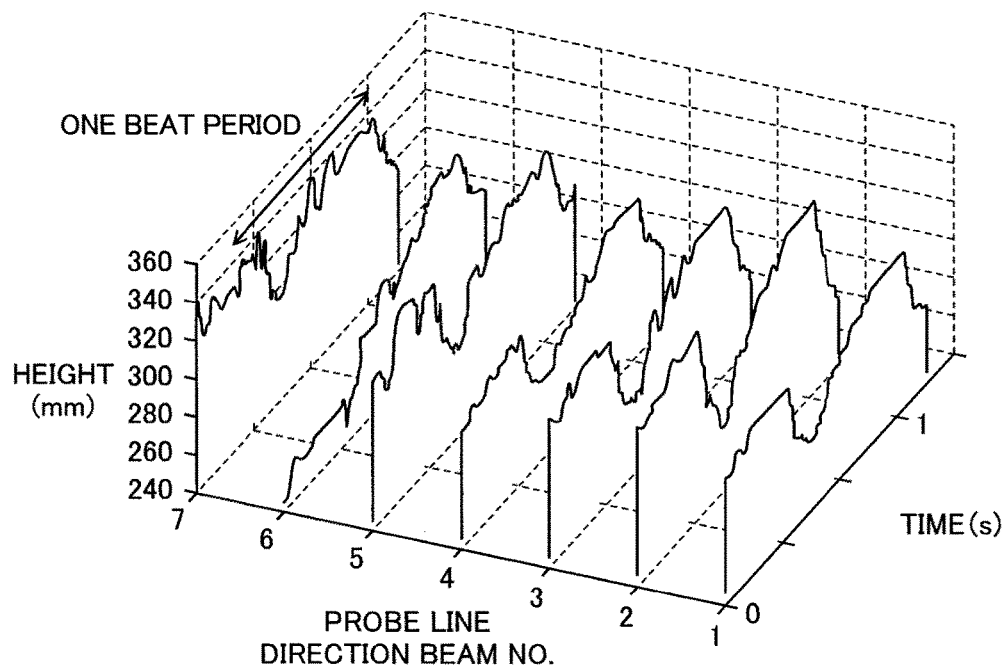
FIG. 15 is a diagram showing yet another display example by the ultrasonic diagnostic device according to the third embodiment of the present invention.

FIG. 15 shows a display example in which, with respect to the ultrasonic tomographic image of a carotid artery that is acquired in the same manner, the surface shape of the vascular lumen-intima boundary 304 set in the subject region to be measured is cut along the measurement position cross section, and the resulting multiple profile lines are arranged in a probe line direction (x-axis direction). FIG. 15 is one in which the height detected by substantially the same one vibrator is represented by the profile lines drawn in the direction of the time axis and which displays how the height of the measurement position to be detected by the vibrator is varied by the pulse.

FIG. 15 shows that the position of the sixth vibrator in the probe line direction, namely, the waveform of beam No. 6 completely differs from other waveforms. It can be estimated that such deformation of the waveform is affected by an artifact resulting from speckles. With a simple B mode image displayed on the x-z plane, information with respect to the direction of the time axis is not obtained; with a simple M mode image displayed two-dimensionally on the z-t plane, the ambient conditions are not identified. As shown in FIG. 15, with the three-dimensional display, by the method of drawing lines between the positions on the probe lines to achieve the display, it is possible to easily estimate the effects of the artifact.

With the data on the lines whose profile is displayed inaccurately due to the effects of the artifact as described above, the stiffness parameter β, the strain rate, the elastic modulus and the like are calculated, with the result that the erroneous values results in an erroneous determination. To overcome the foregoing, with the display method shown in FIG. 15, data that is estimated to be affected by the artifact and the like resulting from the speckles is found and removed, and, with data on highly reliable probe lines and measurement time, elastic indices are calculated. Thus, it is possible to obtain highly reliable elastic indices without being affected by the artifact and the like resulting from the speckles.

Figure 16:
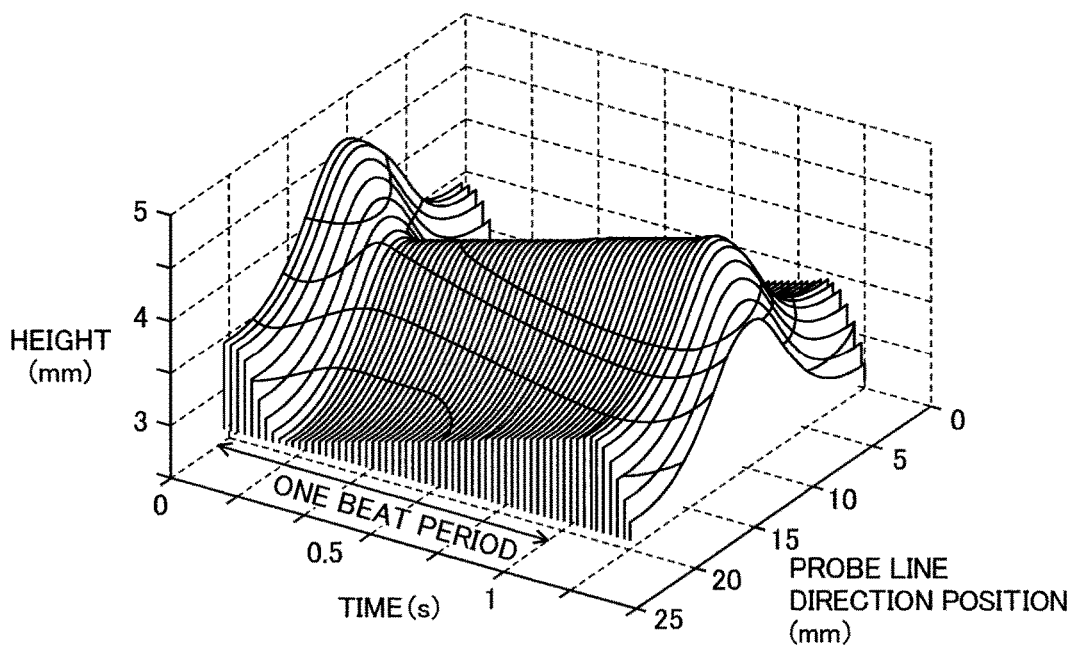
FIG. 16 a diagram showing an example employing a contour line display with respect to the display example of the third embodiment of the present invention.

Accurately reading, from the three-dimensional coordinate display, information on the height of the subject region to be measured requires skills. When the three-dimensional graph is displayed by using different colors corresponding to heights, a height at a given position at given time can be read accurately, and this is convenient. When the color display cannot be used, a contour line display may be used. FIG. 16 is one in which contour lines are introduced into FIG. 11 and this allows the height of each point to be accurately read. When the contour line display is highly learned, it is possible to read the characteristic of the shape from the relationship of the contour lines, line density and the like, and this is convenient.

Although not shown, two or more subject regions to be measured are set, and they may be displayed on one display screen. For example, by displaying two subject regions to be measured, namely, the front intima-vascular lumen boundary and the vascular lumen-rear intima boundary, it is possible to intuitively and accurately understand the expansion and contraction of a blood vessel. When two or more subject regions to be measured are expressed in one image, it is effective to display them by using different colors or different types of line.

Since, in the above description, the features of the present invention are mainly discussed, most of the description of prior art references is omitted. However, for example, the normal B mode image and M mode image and the like can naturally be displayed on the display device. In this way, for example, the image data generation portion 217 has the following function: the image data on the ultrasonic image supplied from the reception circuit 115 is converted (raster conversion) into image data corresponding to the scanning method of the normal television signal, necessary image processing such as gradation processing is performed on the image data and the resulting data is transmitted to the image storage device 219.

By acquiring necessary information from the graph using the method of the present invention, it is possible to calculate the elastic indices such as the stiffness parameter β, the strain rate and the elastic modulus.

Fourth Embodiment

Figure 17:
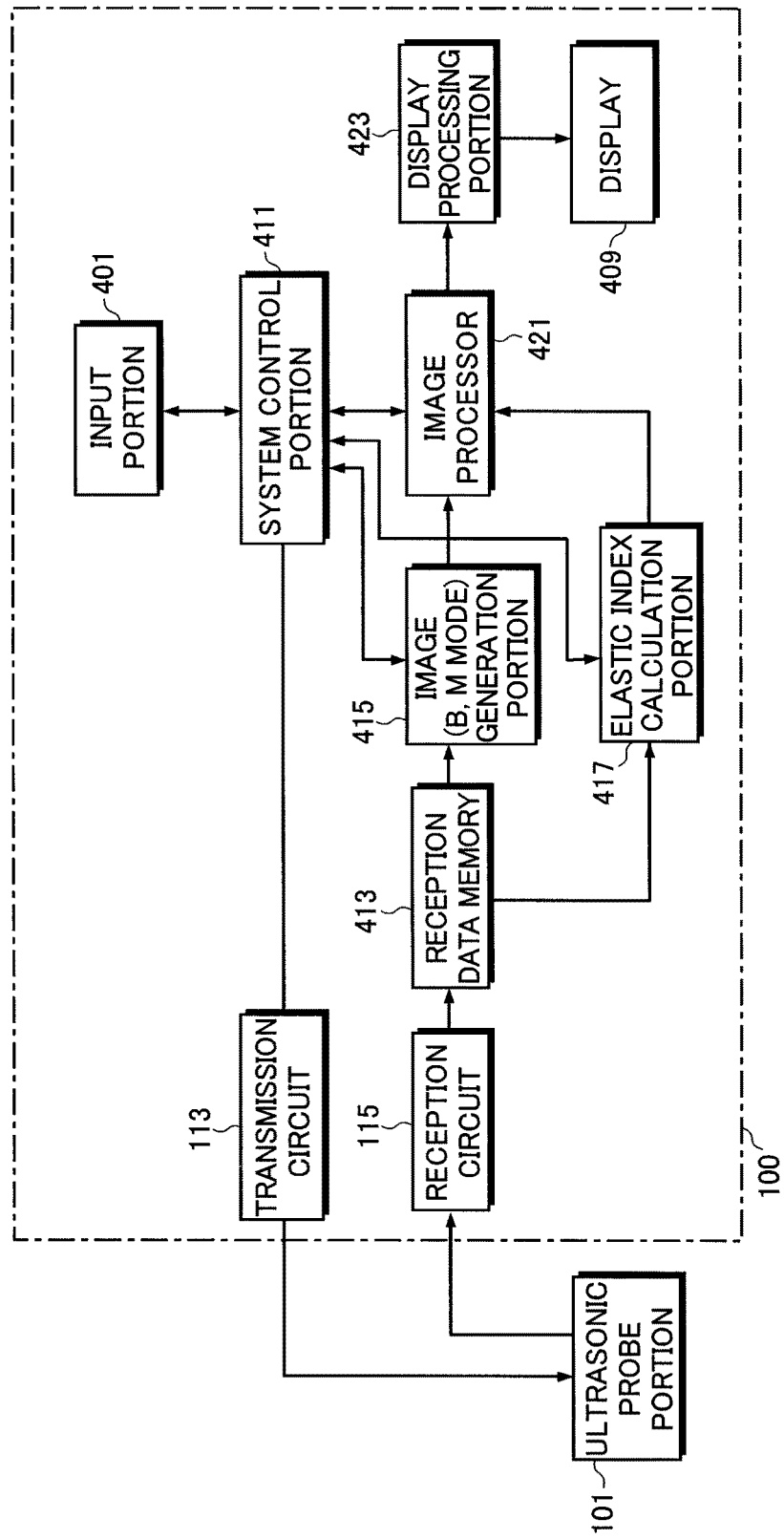
FIG. 17 is a block diagram showing the configuration of an ultrasonic diagnostic device according to a fourth embodiment of the present invention.

FIG. 17 is a block diagram showing a configuration of an ultrasonic diagnostic device according to a fourth embodiment of the present invention, and the same parts as in FIG. 1 are identified with the same symbols, and their description will not be repeated.

The ultrasonic diagnostic device according to the present invention includes the ultrasonic probe portion 101 and the ultrasonic diagnostic device main body 100.

The ultrasonic diagnostic device main body 100 is provided with: an input portion 401, such as a keyboard or a pointing device, that inputs various types of information; the transmission circuit 113 and the reception circuit 115 that control the transmission and reception of ultrasound in the ultrasonic probe 101; a display 407 that displays an image; a system control portion 411 that controls the entire system to adjust the operation appropriately; a reception data memory 413 serving as storage means for storing the reception data output from the reception circuit 115; an image generation portion 415 that generates, based on the reception data, the image data representing the B mode image and M mode image; an elastic index calculation portion 417 that uses the reception data stored in the reception data memory 413 to perform tracking and that calculates target elastic indices; an image processor 421 that forms an image for displaying the image data and the measurement data; and a display processing portion 423 that forms a signal for displaying a screen on the display 407.

The system control portion 411 sequentially sets, through the transmission circuit 113 and the reception circuit 115, a direction in which the ultrasonic probe 101 transmits an ultrasonic beam and a direction in which ultrasonic echo is received, and has both the transmission control function of selecting a transmission delay pattern according to the set transmission direction and the reception control function of selecting a reception delay pattern according to the set reception direction.

In a storage device provided in the system control portion 411, a plurality of types of transmission delay patterns and a plurality of types of reception delay patterns are stored; they are selectively utilized according to the transmission and reception directions.

The transmission circuit 113 has a plurality of channels and generates a plurality of drive signals that are input to a plurality of ultrasonic transducers, respectively. In this case, it is possible to provide, based on the transmission delay pattern selected by the system control portion 411, each delay time for a plurality of drive signals.

The reception circuit 115 has a plurality of channels, receives and amplifies a plurality of analog reception signals output from a plurality of ultrasonic transducers and converts them into digital reception signals. Moreover, the reception circuit 115 provides, based on the reception delay pattern selected by the system control portion 411, each delay time for a plurality of reception signals, and adds those reception signals to perform reception focus processing. This reception focus processing generates a reception signal (reception data) in which the focus of the ultrasonic echo is narrowed.

Then, the reception circuit 115 performs, on the reception data, detection processing such as envelope detection or quadrature detection, and thereafter performs correction for attenuation due to distance by STC (sensitivity time gain control) according to the depth of a location where ultrasound is reflected.

In the quadrature detection processing, ultrasound Φ is multiplied by each of signals cos ωt and sin ωt that have substantially the same angular frequency ω as that of the ultrasound Φ and that are 90 degrees out of phase with each other, and thus down-conversion is performed. The measured reception data contains only a real number component of the ultrasound Φ, but the quadrature detection processing is performed to generate a complex baseband signal V=x+jY.

Specifically, the complex baseband signal V obtained by performing the quadrature detection has an I-phase component (real number component) x and a Q-phase component (imaginary number component) y that are perpendicular to each other, and has information on an amplitude $A=(x^2+y^2)^{1/2}$ and a phase $\theta=\tan^{-1}(y/x)$. Thus, when the quadrature detection is used, it is possible to calculate, based on a larger amount of information, more accurate elastic indices.

The reception data thus processed is sequentially stored in the reception data memory 413 having a memory capacity for storing reception data corresponding to an ultrasonic image equivalent to a plurality of frames. The image generation portion 415 inputs the reception data read from the reception data memory 413, and performs, on the input reception data, the preprocess processing such as log compression or gain adjustment and the scanning line conversion processing for converting the reception data into the image data corresponding to the scanning method of normal television signals to generate an image data and output the generated image data to the image processor 421.

The image processor 421 generates, based on the input image data, elastic indices and the like, the image data representing a screen for displaying the ultrasonic image and the measurement results and the like, and outputs them to the display processing portion 423. The display processing portion 423 generates video signals for displaying the screen, and transmits them to a display 409, and the display 409 displays the screen including the ultrasonic image and the measurement results and the like.

The system control portion 411, the image generation portion 415, the elastic index calculation portion 417, the image processor 421, the display processing portion 423 and the like are formed with the central processing unit (CPU) and software for making the CPU perform various types of processing. The software is stored in a storage portion (not shown). They may be formed with a digital circuit or an analog circuit.

Figure 18:
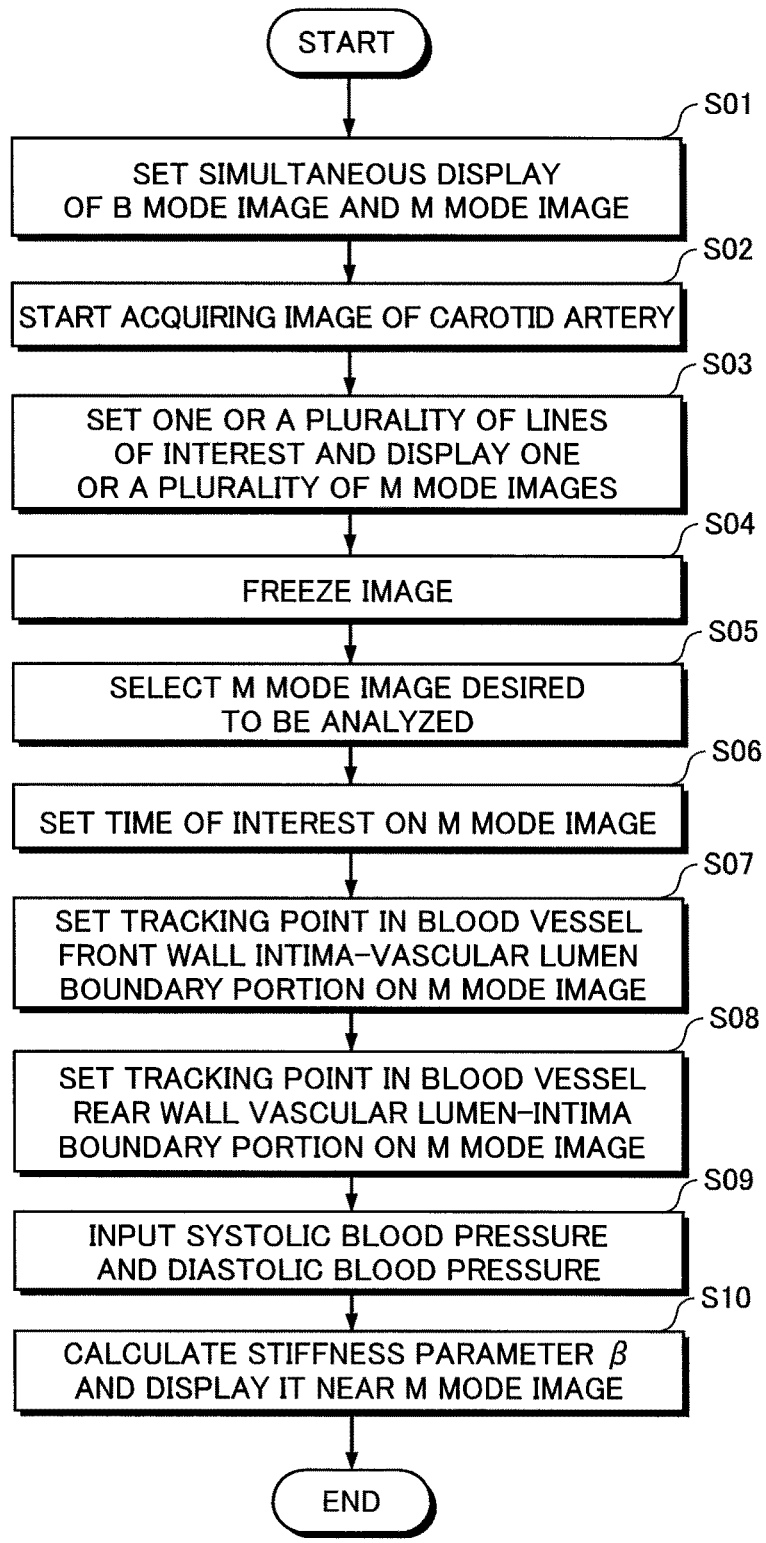
FIG. 18 is a flowchart showing the operation of an ultrasonic diagnostic device according to the fourth embodiment.

FIG. 18 is a flowchart showing the operation of the ultrasonic diagnostic device according to this embodiment as an example that is the case where the stiffness parameter β is calculated. When the operator sets to display the B mode image and the M mode image together through the input portion 401 (step S01), the system control portion 411 controls the transmission circuit 113 and the reception circuit 115 to operate the ultrasonic probe 101 pressed onto a neck, and acquires the ultrasonic image of a carotid artery for only a predetermined period of time.

The transducer array of the ultrasonic probe 101 is arranged such that, for example, the scanning direction coincides with a direction in which the blood of the carotid artery flows, and receives ultrasonic echo from the front wall of a blood vessel and the blood vessel wall of the rear wall to output the reception signal. The reception circuit 115 generates, based on the reception signal output from the ultrasonic probe 101, reception data, and a predetermined amount of the reception data generated by the reception circuit 115 is stored in the reception data memory 413.

Then, the image generation portion 415 starts to acquire, from the reception data memory 413, the reception data corresponding to the ultrasonic image of the carotid artery (step S02), and generates B mode image data serving as tomographic image information on a tissue within the body under test to display, through the image processor 421 and the display processing portion 423, the B mode image on the display 409.

The operator such as a doctor finds, from one or a plurality of B mode images displayed, some line positions where the reception data is stable over each screen, and operates the input portion 401 to set one or a plurality of lines of interest (step S03). The line of interest can be set by utilizing a pointing device or the like displayed together with the image. Preferably, the position of the line of interest that is set is clearly displayed by a vertical line or the like superimposed on the image. For convenience, one B mode image may only be displayed such that a portion where the reception data is stable is found.

The image generation portion 415 reads, for each line of interest that is set, the reception data in the position corresponding to the line of interest over a predetermined period from the reception data memory 413, sequentially generates the M mode image data over the predetermined period along the time axis and displays, through the image processor 421 and the display processing portion 423, one or a plurality of M mode images corresponding to the line of interest on the display 409 (step S03). When the operator finds, while the displayed image changes over time, an appropriate screen that is likely to be utilized for analysis, the operator operates the input portion 401 to transmit an instruction signal to the system control portion 411 to freeze the screen of the M mode image (step S04).

Figure 19:
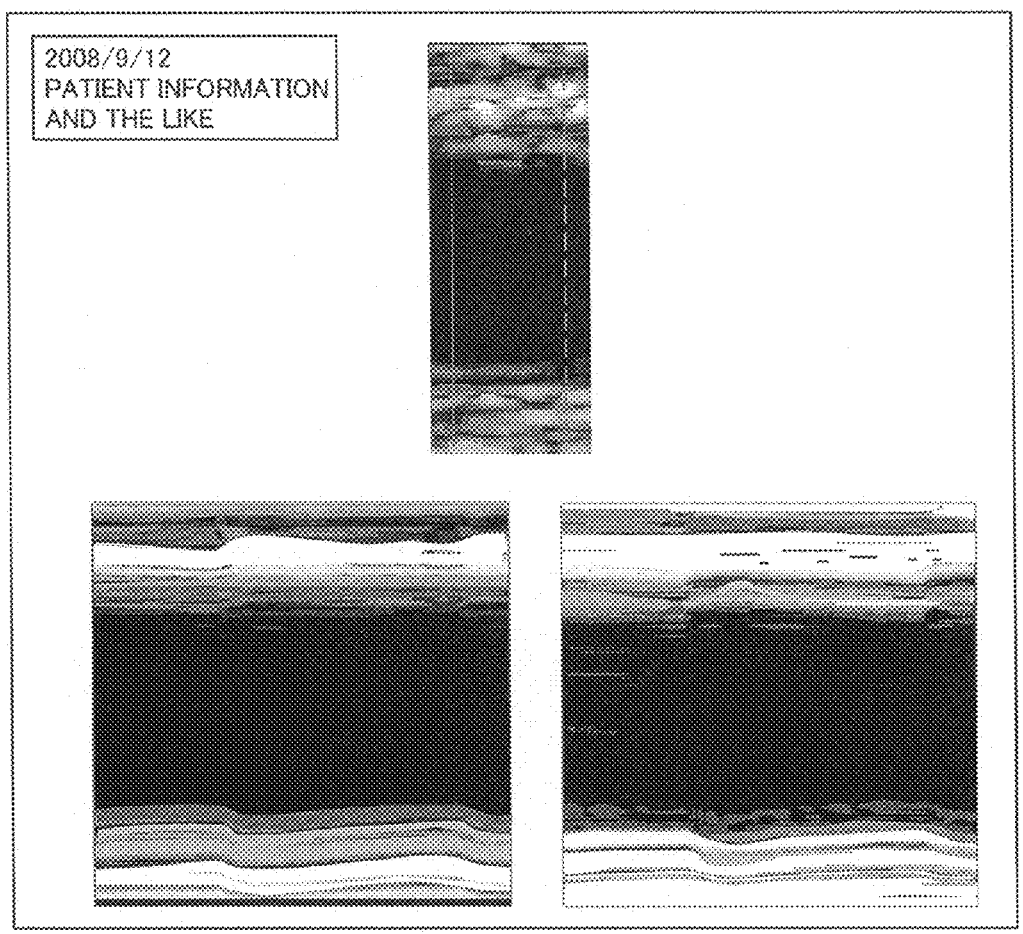
FIG. 19 is a diagram showing an example of an image when the image is frozen in the fourth embodiment.

FIG. 19 is a figure in which the subject to be measured is the front wall and the rear wall of the carotid artery, and shows an example of an image on the display 409 when the image is frozen. In FIG. 19, one B mode image is displayed in the upper side, and two M mode images are displayed in the lower side. In the B mode image, two lines of interest are set; the M mode image on the left side is generated from the reception data in the line of interest indicated by a solid line, and the M mode image on the right side is generated from the reception data in the line of interest indicated by a broken line. In the upper left corner of the screen, information such as measurement conditions is displayed.

In the M mode image on the right side, an unstable portion is found to be in the inner wall; the M mode image on the left side is a high-quality image that has only a small amount of noise and that is likely to be utilized for analysis. Although, in FIG. 19, the M mode image equivalent to about one beat is only displayed, in order for an easy determination to be made, the M mode image equivalent to three beats is more preferably displayed. The B mode image displayed when the screen is frozen may be displayed when the freeze button is pressed or may be displayed anytime in a predetermined one beat.

When a plurality of M mode images are displayed, the image is frozen, and thereafter the operator operates the input portion 401 to select the M mode image used in the elastic index measurement (step S05). When the M mode image to be utilized is determined, the image generation portion 415 enlarges the M mode image to display it on the display 409 and reduces other images to display them on the display 409.

Then, the operator specifies, in the M mode image, a tracking start time and a tracking completion time to set a time-of-interest range (step S06). Moreover, the operator sets, in a blood vessel front wall intima-vascular lumen boundary portion in the M mode image, a tracking point (step S07), and furthermore sets, in a blood vessel rear wall vascular lumen-intima boundary portion, a tracking point (step S08). As a tracking portion, at least one of a boundary between an adventitia and a media in a blood vessel front wall, a boundary between an intima and a vascular lumen in the blood vessel front wall, a boundary between the vascular lumen and the intima in a blood vessel rear wall and a boundary between the media and the adventitia in the blood vessel rear wall can be included.

Figure 20:
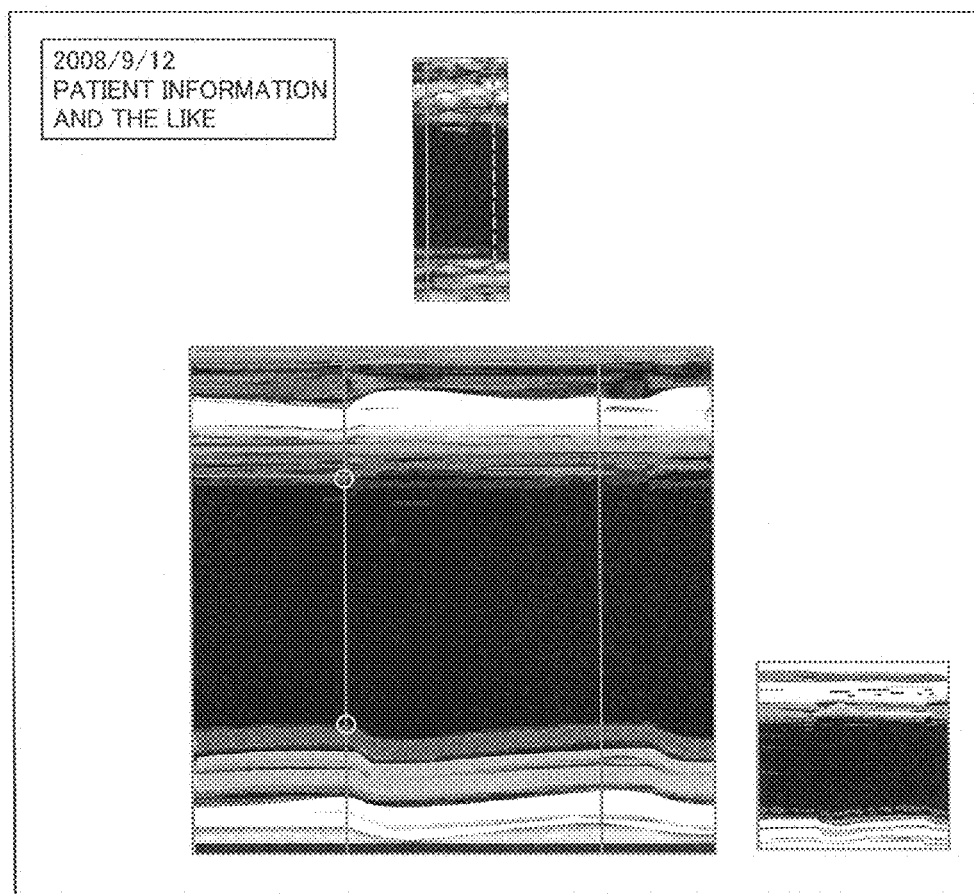
FIG. 20 is a display screen showing a state in which a time of interest and a tracking point are set in an M mode image in the fourth embodiment.

FIG. 20 is a display screen of the display 409 showing a state in which the time of interest and the tracking point are set in the M mode image. Since, on the display screen used when the time of interest is set, the B mode image at a set time is displayed in real time, it is possible to check noise conditions.

Moreover, the operator operates the input portion 401 to input the maximum blood pressure and the minimum blood pressure measured with the cuff-type blood pressure meter (step S09). These blood pressure values are utilized as the contracting period blood pressure Ps and the expanding period blood pressure Pd. In response to this, the elastic index calculation portion 417 tracks, from the set tracking point, a brightness variation point characterizing the intima-vascular lumen boundary to perform the tracking. The tracking can be performed by various methods such as a tomographic image pattern matching method, a zero cross point method, a tissue Doppler method and a phase difference tracking method with the subject point being defined; it is needless to say that any method may be employed.

During the tracking of the specified region, the elastic index calculation portion 417 determines the systolic maximum blood vessel diameter Ds and the diastolic minimum blood vessel diameter Dd to calculate the stiffness parameter β from the following equation:

$$\beta = [\text{Log}(Ps/Pd)]/(Ds/Dd - 1)$$

The calculation result of the stiffness parameter β is displayed near the M mode image in the display screen (step S10).

Figure 21:
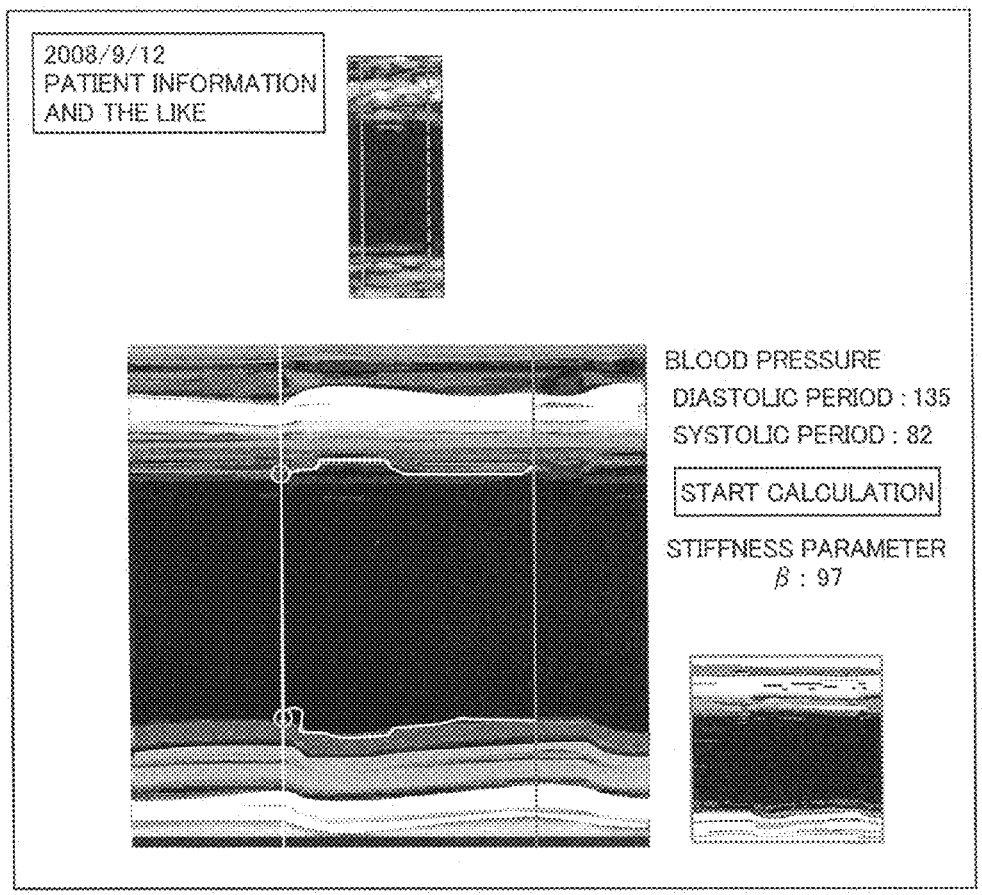
FIG. 21 is a display screen in which a stiffness parameter β is displayed in the fourth embodiment.

FIG. 21 shows a display screen in which the stiffness parameter β is displayed by inputting the systolic blood pressure Ps and the diastolic blood pressure Pd. In the M mode image, paths are displayed that are produced by tracking the intima-vascular lumen boundary on the front wall and the rear wall of a blood vessel. The input blood presser and the calculated stiffness parameter β are displayed in values. Furthermore, the arteriosclerosis risk and the age of a blood vessel may be calculated and displayed.

Figure 22:
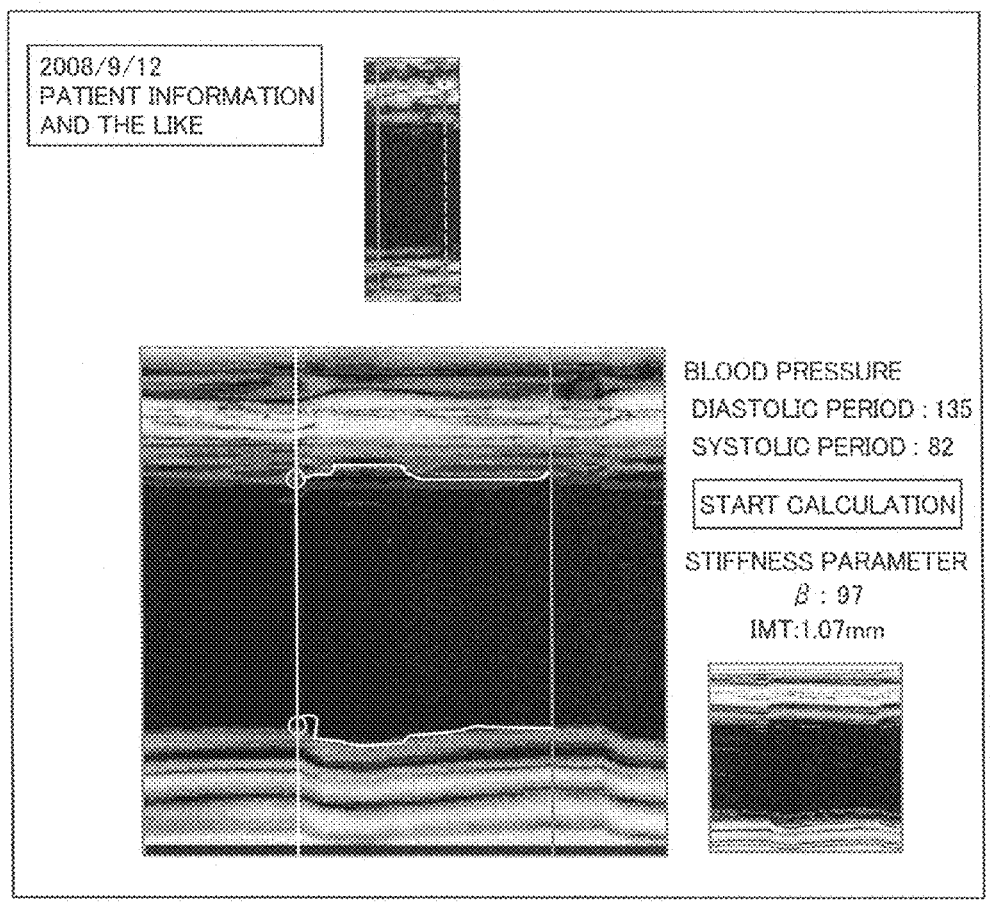
FIG. 22 is a display screen in which the IMT is further displayed in the fourth embodiment.

By the use of information on the set tracking portion, the IMT (intima media thickness), the blood vessel diameter, the ratio between the minimum blood vessel diameter and the maximum blood vessel diameter and the like may be calculated and displayed on the display portion together with the elastic indices. FIG. 22 shows an example of a display screen in which an IMT value determined from the information on the tracking portion at the time of interest shown together with the M mode image is additionally written.

Although it is generally thought that it is difficult to stably acquire the elastic indices of a tissue moving in synchronization with the pulse of a hear or the like, according to the ultrasonic diagnostic device of this embodiment, elastic indices are calculated from reception data at a place selected as a highly reproducible location, and thus it is possible to stably obtain elastic indices on a blood vessel and the like.

According to the present invention, it is possible to provide a display screen that functions as such a convenient interface that, before starting the tracking for calculating elastic indices in the ultrasonic diagnostic device, an operator such as a doctor determines whether or not reliable elastic indices can be obtained from data and selects an appropriate data portion. With the ultrasonic diagnostic device of the present invention, since elastic indices such as an elastic modulus that are difficult to stably acquire are determined through the decision and selection of a doctor or the like, it is possible to obtain a more reliable result than conventionally obtained.

Although, in the ultrasonic diagnostic device of this embodiment, one M mode image is selected, as the line of interest, from the M mode images equivalent to two lines, and the elastic index is determined, highly continuous two or three lines are selected from about five candidate lines, and the elastic index is calculated, and their average values may be used as the elastic index of a blood vessel. In this case, five M mode images are displayed, and, among them, two or three M mode images are selected and the stiffness parameter β is determined, with the result that, on an instruction screen, the stiffness parameter β of each of the M mode images and the stiffness parameter β determined by the averaging are displayed.

Although, in the ultrasonic diagnostic device of this embodiment, the stiffness parameter β is used as the elastic index, a strain rate or an elastic modulus can be selected as the elastic index. When the strain rate and the elastic modulus are calculated, since the thickness of a blood vessel wall, especially IMT (intima media thickness), is an issue, as shown in FIG. 3, the tracking point is set in the following four locations: a boundary between an adventitia and a media in a blood vessel front wall, a boundary between an intima and a vascular lumen in the blood vessel front wall, a boundary between the vascular lumen and the intima in a blood vessel rear wall and a boundary between the media and the adventitia in the blood vessel rear wall. Minute variations in blood vessel thickness are measured from the measurement values obtained by tracking the adventitia-media boundary and the intima-vascular lumen boundary in each of the front wall and the rear wall, and thus the maximum value Td and the minimum value Ts of the blood vessel thickness are determined.

By using these values, the strain rate can be determined from "(Td−Ts)/Td." The elastic modulus E can be determined from "E=(Ps−Pd)/[(Td−Ts)/Td]." When a more advanced algorism is used, the area between the adventitia-media boundary and the intima-vascular lumen boundary in each of the front wall and the rear wall is further divided into a plurality of pieces, and the elastic modulus of each region may be measured. The elastic index calculation portion 417 calculates, for the set tracking portion, at least one of the IMT, the blood vessel diameter and the ratio of the minimum blood vessel diameter to the maximum blood vessel diameter, and the result may be displayed on the display 409 together with the elastic indices.

Although, in the ultrasonic diagnostic device of this embodiment, the position information is displayed on the horizontal axis in the M mode image, speed information may be displayed. In this case, it is preferable to set the tracking point on the B mode image or to together display the M mode image including the position information to set the tracking point.

Figure 23:
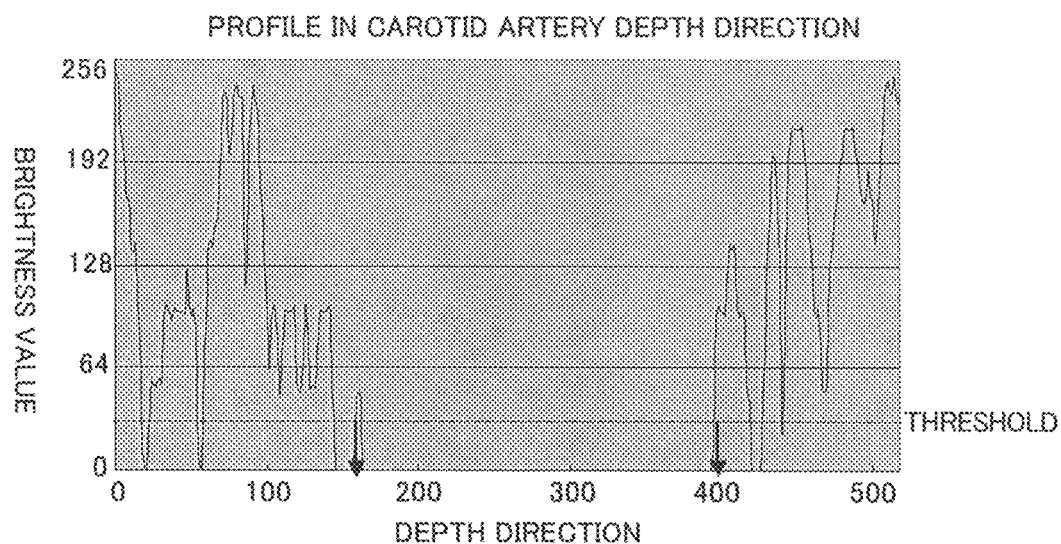
FIG. 23 is a diagram showing an example of brightness profile at the time of interest in the fourth embodiment.

The setting of the tracking point can be automatically performed by the use of brightness profile at the time of interest selected in the M mode image. FIG. 23 shows brightness profile at the time of interest set in FIG. 20 in the depth direction of the reception data. The left edge of the figure is the position of a probe; it is deeper as it extends rightward.

Figure 24:
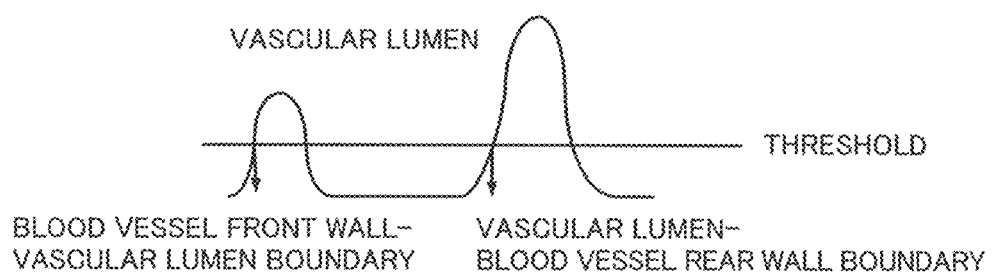
FIG. 24 is a line diagram showing a method of automatically determining the tracking point in the fourth embodiment.

FIG. 24 is a line diagram showing a method of automatically determining the tracking point. The vascular lumen-blood vessel front wall boundary to be selected as the tracking point can be determined at the point at which, when it is followed from the position of the vascular lumen detected as a black-removed portion of the center portion toward the direction of the probe, the brightness exceeds a threshold, further exceeds the top portion and then reaches the threshold. On the other hand, the vascular lumen-blood vessel rear wall boundary can be determined at the point at which, when it is followed from the center portion toward the direction of the deeper portion, the brightness reaches the threshold. Although, in the figure, the same threshold is used, the front wall boundary and the rear wall boundary may be determined with different thresholds.

Fifth Embodiment

An ultrasonic diagnostic device according to a fifth embodiment of the present invention has a function of highly accurately measuring the amount of displacement of a body tissue moving at a regular period in synchronization with a pulse of a body under test to calculate, from the amount of displacement, elastic characteristics, and also has the function of detecting, from a reception signal between an ultrasonic probe and the body tissue, the displacement (the hand shake of an examiner and the body shake of the body under test) of the relative position between the ultrasonic probe and the body under test to estimate, with the amount of displacement of the relative position, the accuracy of the elastic characteristic calculated by the above-mentioned function. The body tissue mentioned here refers to, for example, a blood vessel, a heart or a carotid artery.

Figure 25:
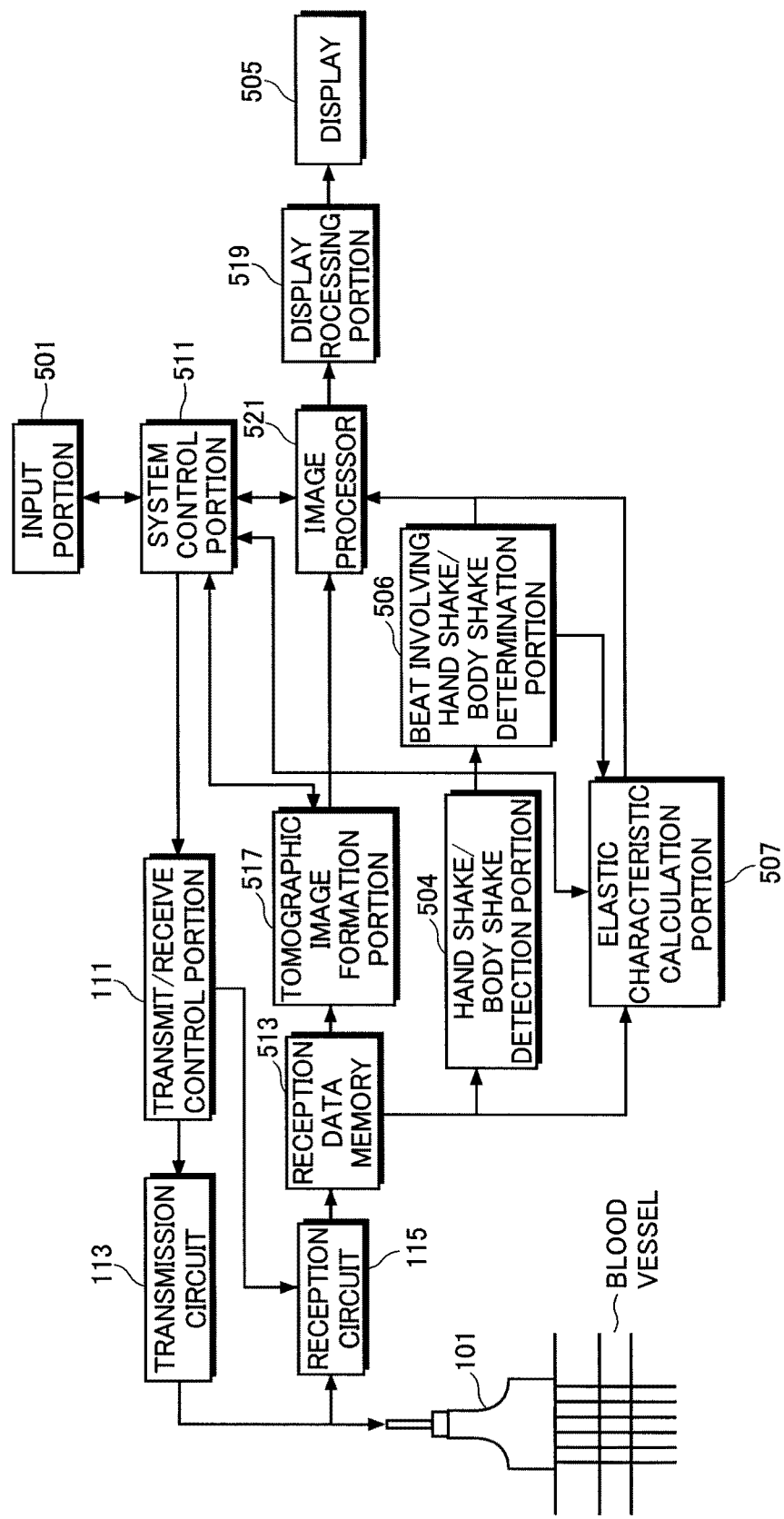
FIG. 25 is a block diagram showing the configuration of an ultrasonic diagnostic device capable of measuring elastic indices and according to a fifth embodiment of the present invention.

FIG. 25 is a block diagram showing the configuration of an ultrasonic diagnostic device capable of measuring elastic indices and according to the fifth embodiment of the present invention, and the same parts as in FIG. 1 are identified with the same symbols, and their description will not be repeated.

The ultrasonic diagnostic device according to this embodiment includes the ultrasonic probe 101 incorporating a plurality of ultrasonic transducers that transmit and receive ultrasound and the ultrasonic diagnostic device main body.

The ultrasonic diagnostic device main body is provided with: an input portion 501, such as a keyboard or a pointing device, that inputs various types of information; the transmission circuit 113 and the reception circuit 115 that control the transmission and reception of ultrasound in the ultrasonic probe 101; the transmit/receive control portion 111; a display 505 that displays an image; a system control portion 511 that controls the entire system to adjust the operation appropriately; a reception data memory 513 serving as storage means for storing the reception data output from the reception circuit 115; a tomographic image formation portion 517 that generates, based on the reception data, image data representing the B mode image and the M mode image; a hand shake/body shake detection portion 504 that detects hand shake and body shake with the reception data stored in the reception data memory 513; a beat involving hand shake/body shake determination portion 506; an elastic characteristic calculation portion 507 that uses the reception data stored in the reception data memory 513 to perform tracking and that calculates target elastic characteristic; an image processor 521 that forms an image for displaying the image data and the measurement data; and a display processing portion 519 that forms a signal for displaying a screen on the display 505.

In a storage device provided in the system control portion 111, a plurality of types of transmission delay patterns and a plurality of types of reception delay patterns are stored; they are selectively utilized according to the transmission and reception directions.

The transmission circuit 113 has a plurality of channels and generates a plurality of drive signals that are input to a plurality of ultrasonic transducers, respectively.

The reception circuit 115 has a plurality of channels, receives and amplifies a plurality of analog reception signals output from a plurality of ultrasonic transducers and converts them into digital reception signals.

Then, the reception circuit 115 performs, on the reception data, detection processing such as envelope detection or quadrature detection, and thereafter performs correction for attenuation due to distance by STC (sensitivity time gain control) according to the depth of a location where ultrasound is reflected.

In the quadrature detection processing, ultrasound is multiplied by each of signals cos ωt and sin ωt that have substantially the same angular frequency ω as that of the ultrasound Φ and that are 90 degrees out of phase with each other, and thus down-conversion is performed. The measured reception data contains only a real number component of the ultrasound Φ, but the quadrature detection processing is performed to generate a complex baseband signal V=x+ jY.

Specifically, the complex baseband signal V obtained by performing the quadrature detection has an I-phase component (real number component) x and a Q-phase component (imaginary number component) y that are perpendicular to each other, and has information on an amplitude $A=(x^2+y^2)^{1/2}$ and a phase $\theta=\tan^{-1}(y/x)$. Thus, when the quadrature detection is used, it is possible to calculate, based on a larger amount of information, more accurate elastic characteristics.

The reception data thus processed is sequentially stored in the reception data memory 513 having a memory capacity for storing reception data corresponding to an ultrasonic image equivalent to a plurality of frames.

The tomographic image formation portion 517 inputs the reception data read from the reception data memory 513, and performs, on the input reception data, the preprocess processing such as log compression or gain adjustment and the scanning line conversion processing for converting the reception data into the image data corresponding to the scanning method of normal television signals to generate an image data and output the generated image data to the image processor 521.

The hand shake/body shake detection portion 504 inputs the reception data read from the reception data memory 513, and detects, with the input reception data, the hand shake of the examiner and the body shale of the body under test.

The beat involving hand shake/body shake determination portion 506 determines, with the reception data including the hand shake of the examiner and the body shale of the body under test detected by the hand shake/body shake detection portion 504, the accuracy of the reception data, and outputs the determined information to the image processor 521.

The elastic characteristic calculation portion 507 inputs the reception data read from the reception data memory 513, calculates the elastic characteristics with the input reception data and outputs the calculated elastic characteristics to the image processor 521.

The image processor 521 generates, based on the input image data, information on the hand shake or the body shake, elastic characteristic data and the like, image data representing a screen for displaying the ultrasonic image, the measurement results and the like, and outputs it to the display processing portion 519. The display processing portion 119 generates a video signal for displaying the screen to transmit it to the display 505; the display 505 displays the screen including the ultrasonic image, the measurement results and the like.

The system control portion 511, the tomographic image formation portion 517, the hand shake/body shake detection portion 504, the beat involving hand shake/body shake determination portion 506, the elastic characteristic calculation portion 507, the image processor 521, the display processing portion 519 and the like are formed with the central processing unit (CPU) and software for making the CPU perform various types of processing. The software is stored in a storage portion (not shown). They may be formed with a digital circuit or an analog circuit.

FIG. 18 is a flowchart showing the operation of the ultrasonic diagnostic device according to this embodiment as an example of the calculation of the elastic characteristics that is the case where the stiffness parameter β is calculated. When the operator (examiner) sets to display the B mode image and the M mode image together through the input portion 501 (step S01), the system control portion 511 controls the transmission circuit 113 and the reception circuit 115 to operate the ultrasonic probe 101 pressed onto a neck, and acquires the ultrasonic image of a carotid artery for only a predetermined period of time.

The transducer array of the ultrasonic probe 101 is arranged such that, for example, the scanning direction coincides with a direction in which the blood of the carotid artery flows, and receives ultrasonic echo from the front wall of a blood vessel and the blood vessel wall of the rear wall to output the reception signal. The reception circuit 115 generates, based on the reception signal output from the ultrasonic probe 101, reception data, and a predetermined amount of the reception data generated by the reception circuit 115 is stored in the reception data memory 513.

Then, the tomographic image formation portion 517 starts to acquire, from the reception data memory 513, the reception data corresponding to the ultrasonic image of the carotid artery (step S02), and generates B mode image data serving as tomographic image information on a tissue within the body under test to display, and displays the B mode image, through the image processor 521 and the display processing portion 519, on the display 505. Here, whether or not the B mode image is an image including the hand shake or the body shake is checked by the hand shake/body shake detection portion 504 and the beat involving hand shake/body shake determination portion 506. This determination method will be described in detail with reference to FIGS. 26 to 29.

Figure 26:
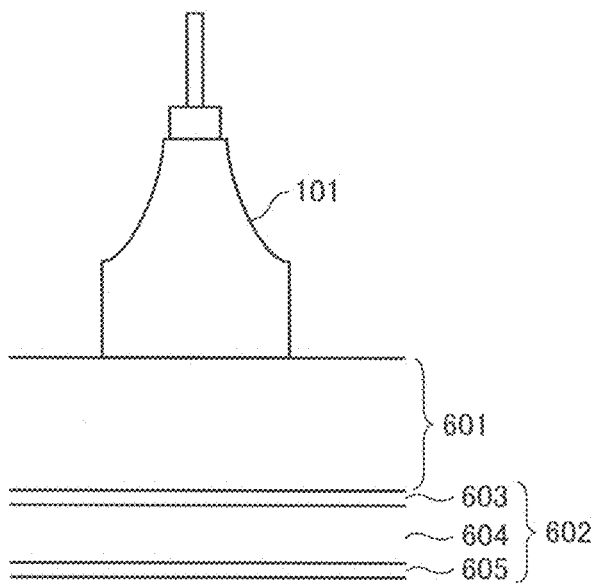
FIG. 26 is a conceptual diagram showing a method of detecting hand shake or body shake.

FIG. 26 is a conceptual diagram showing a method of detecting hand shake or body shake. The examiner presses the ultrasonic probe 101 onto, for example, the neck of the person to be tested to obtain a reception signal from an area 601 between the ultrasonic probe 101 and a blood vessel 602, and the reception signal is stored in the reception data memory 513. Then, the hand shake of the examiner and the body shake of the person to be tested are detected from the reception data read from the reception data memory 513, and, with the reception data including the detected hand shake and the like, the reliability (accuracy) of the reception signal is determined (estimated).

As shown in FIG. 26, the blood vessel 602 has a blood vessel front wall 603, a blood vessel rear wall 605 and a vascular lumen 604 located between the blood vessel front wall 603 and the blood vessel rear wall 605. Since, in order to highly accurately detect the elastic characteristic of the blood vessel wall, it is necessary to highly accurately measure variations in the diameter of the blood vessel and the thickness of the blood vessel wall, information on the reliability of the reception signal is useful.

Figure 27:
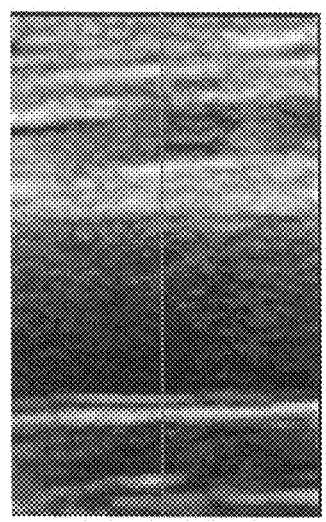
FIG. 27 is a diagram showing the B mode image of a carotid artery.

FIG. 27 is a diagram showing the B mode image of a carotid artery. This B mode image is a B mode image displayed on the above-mentioned display 505. In the B mode image, the blood vessel front wall 603, the vascular lumen 604 and the blood vessel rear wall 605 as shown in FIG. 26 are displayed.

Figure 28:
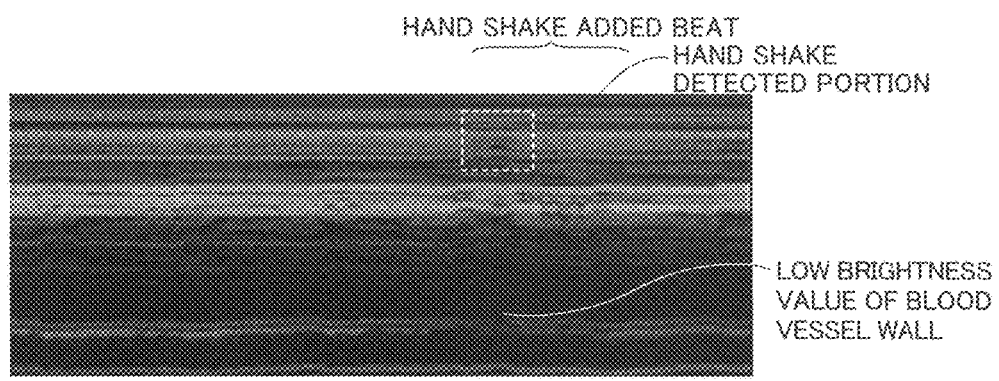
FIG. 28 is a diagram showing the M mode image of a vertical line shown in FIG. 27.

FIG. 28 is a diagram showing the M mode image of a vertical line shown in FIG. 27. In the M mode image, a hand shake is added at the fourth beat. On the hand shake, the brightness value of the blood vessel rear wall is low, and it is understood that it is impossible to highly accurately measure the amount of displacement of the blood vessel rear wall.

Figure 29:
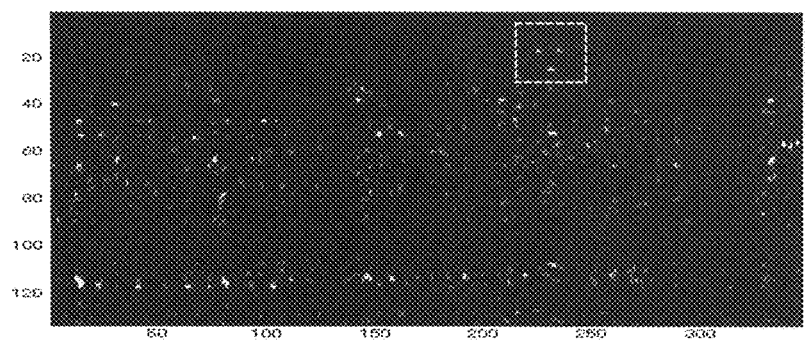
FIG. 29 is a diagram showing an image obtained by removing difference between frames from the M mode image shown in FIG. 28.

FIG. 29 shows an image obtained by removing, from the M mode image shown in FIG. 28, the difference between frames that are continuous in terms of time, by performing filter processing and by adjusting the brightness. FIG. 28 shows that, since the blood vessel portion is always moving by the pulsation, it is difficult to recognize the hand shake, but since a tissue portion (corresponding to the reference numeral 201 shown in FIG. 26) between the blood vessel portion and the probe is stationary, the hand shake is easily recognized, and, in the tissue portion, the SN ratio is significantly excellent, and thus a hand shake portion and a hand shape pulse can be detected. Here, the hand shake is detected by the difference image between frames; however, even when the hand shake is detected by the pattern matching method or the like, since there is little noise in the tissue portion between the blood vessel portion and the probe due to the moving of the tissue portion, the hand shake can be desirably detected.

The processing shown in FIGS. 27 to 29 is performed by the hand shake/body shake detection portion 504. Specifically, in the hand shake/body shake detection portion 504, as shown in FIG. 29, the difference between frames is measured and the hand shake is detected from the difference image. In this way, it is possible to detect that data at the fourth beat in the M mode image shown in FIG. 28 includes the hand shake. Then, from the reception data including the detected hand shake and the like, the amount of displacement of the relative position between the ultrasonic probe 200 and the body under test is detected, and the reliability (accuracy) of the reception signal is determined (estimated) by the determination portion 506 from the detected amount of displacement (in other words, the amount of hand shake and body shake). The amount of displacement of the relative position mentioned here is equivalent to the amount of displacement between the position of the tissue in the hand shake detection portion at the fourth beat shown in FIG. 4 and the position of the corresponding tissue at hand shake-free beats (the first, second and third beats); the amount of displacement can be detected from the M mode image shown in FIG. 28.

The determination method by the determination portion 506, for example, is that, if the detected amount of displacement of the relative position is equal to or more than a predetermined threshold, the received data is determined to be the reception data at the beat in which the hand shake or the body shake occurs, whereas, if the amount of displacement is less than the predetermined threshold, the received data is determined to be the reception data at the beat in which no hand shake or body shake occurs. As the predetermined threshold, the displacement of the relative position is preferably set at 0.1 mm. This is because: the center frequency of ultrasound is about 1 to 15 MHz, and, in particular, it is considered to be typically 7.5 MHz, and, when it is converted into a wavelength, it is about 0.2 mm; when the hand shake is less than a half wavelength (0.1 mm), it is unlikely to receive effects of aliasing, and the measurement of the elastic characteristics is unlikely to be affected by it.

The examiner such as a doctor finds, from one or a plurality of B mode images displayed, some line positions where the reception data is stable over each screen, and operates the input portion 501 to set one or a plurality of lines of interest (step S03). The line of interest can be set by utilizing a pointing device or the like displayed together with the image. Preferably, the position of the line of interest that is set is clearly displayed by a vertical line or the like superimposed on the image. For convenience, one B mode image may only be displayed such that a portion where the reception data is stable is found.

The tomographic image formation portion 517 reads, for each line of interest that is set, the reception data in the position corresponding to the line of interest over a predetermined period from the reception data memory 513, sequentially generates the M mode image data over the predetermined period along the time axis and displays, through the image processor 521 and the display processing portion 523, one or a plurality of M mode images corresponding to the line of interest on the display 507 (step S03). When the examiner finds, while the displayed image changes over time, an appropriate screen that is likely to be utilized for analysis, the examiner operates the input portion

501 to transmit an instruction signal to the system control portion 511 to freeze the screen of the M mode image (step S04).

Figure 30:
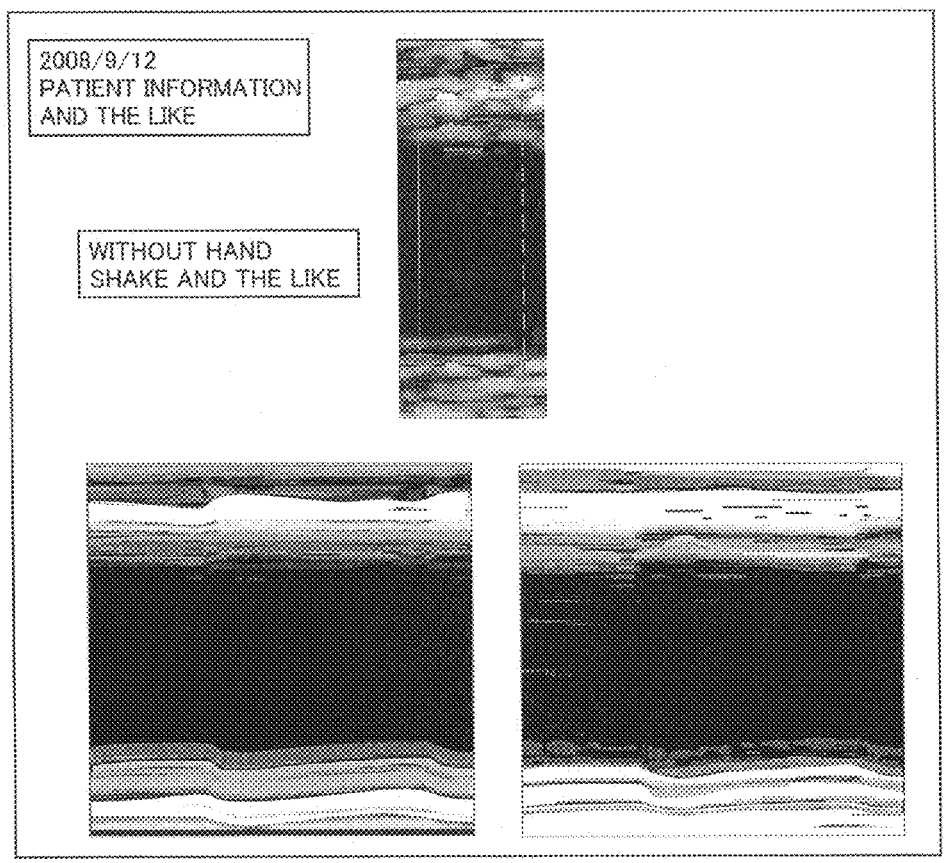
FIG. 30 a diagram showing, when a subject to be measured is the front wall and the rear wall of a carotid artery, an example of an image on a display at the time of the image being frozen.

FIG. 30 is a figure in which the subject to be measured is the front wall and the rear wall of the carotid artery, and shows an example of an image on the display 505 when the image is frozen. In FIG. 30, one B mode image is displayed in the upper side, and two M mode images are displayed in the lower side. In the B mode image, two lines of interest are set; the M mode image on the left side is generated from the reception data in the line of interest indicated by a solid line, and the M mode image on the right side is generated from the reception data in the line of interest indicated by a broken line. In the upper left corner of the screen, information such as measurement conditions is displayed. If, in the M mode image displayed, there is an image in which the hand shake or the body shake occurs, a display indicating it is displayed on the screen; if there is no image in which the hand shake or the body shake occurs, a display indicating it is displayed on the screen. In addition, an alarm may be sounded to notify the examiner of whether or not the hand shake or the body shake is present. If a display indicating the image where the hand shake or the like occurs (in other words, the hand shake or the like occurs) is displayed, the operations from step S02 to step S04 shown in FIG. 18 are repeated. The M mode image in which the hand shake or the like occurs is used, and thus the elastic characteristics are measured, with the result that the accuracy of the elastic characteristics is low.

In the M mode image on the right side, an unstable portion is found to be in the inner wall; the M mode image on the left side is a high-quality image that has only a small amount of noise and that is likely to be utilized for analysis. Although, in FIG. 30, the M mode image equivalent to about one beat is only displayed, in order for an easy determination to be made, the M mode image equivalent to three beats is more preferably displayed. The B mode image displayed when the screen is frozen may be displayed when the freeze button is pressed or may be displayed anytime in a predetermined one beat.

When a plurality of M mode images are displayed, the image is frozen, and thereafter the examiner operates the input portion 501 to select the M mode image used in the elastic index measurement (step S05). In this case, in each M mode image, a display indicating whether or not the hand shake or the body shake is present is displayed, and the examiner may select the M mode image in which there is no hand shake or the like, and the M mode image in which the hand shake or the like is present may fail to be displayed. When the M mode image to be utilized is determined, the tomographic image formation portion 517 enlarges the M mode image to display it on the display 505 and reduces other images to display them on the display 105.

Then, the examiner specifies, in the M mode image, a tracking start time and a tracking completion time to set a time-of-interest range (step S06). Moreover, the examiner sets, in a blood vessel front wall intima-vascular lumen boundary portion in the M mode image, a tracking point (step S07), and furthermore sets, in a blood vessel rear wall vascular lumen-intima boundary portion, a tracking point (step S08). As a tracking portion, at least one of a boundary between an adventitia and a media in a blood vessel front wall, a boundary between an intima and a vascular lumen in the blood vessel front wall, a boundary between the vascular lumen and the intima in a blood vessel rear wall and a boundary between the media and the adventitia in the blood vessel rear wall can be included.

Figure 31:
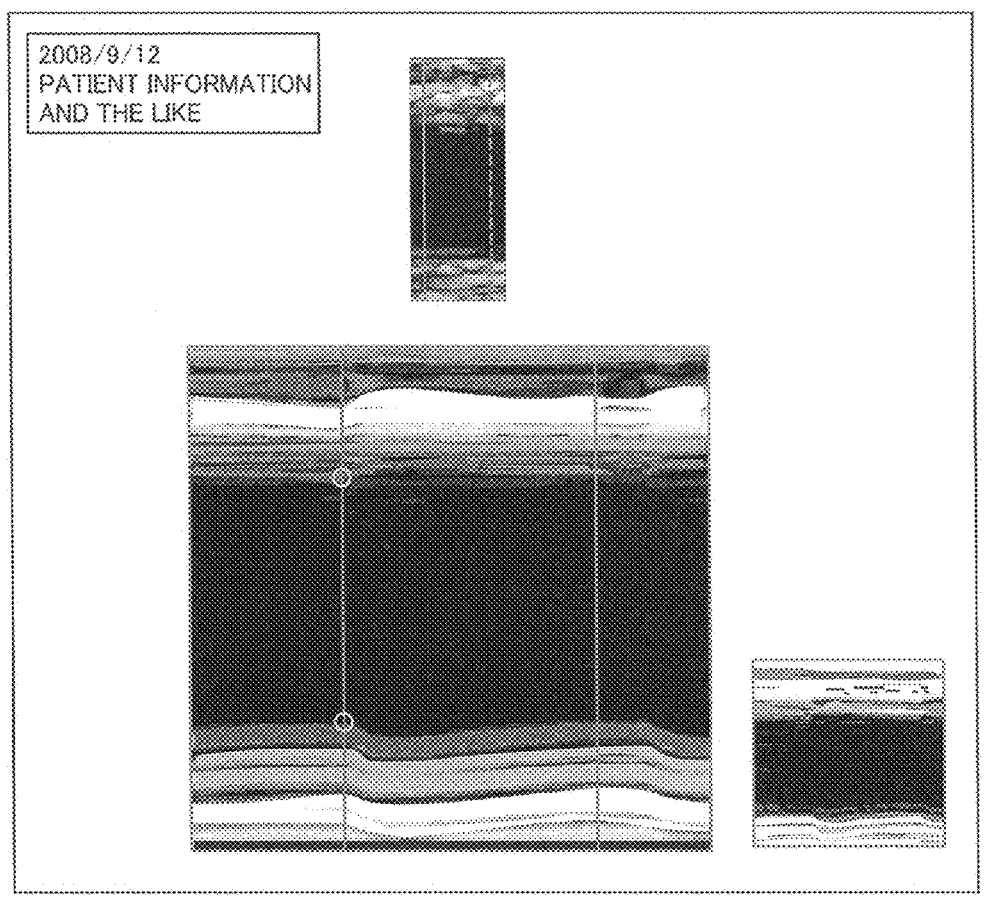
FIG. 31 is a display screen of the display showing the state in which, in the M mode image, the time of interest is set and the tracking point is set.

FIG. 31 is a display screen of the display 505 showing a state in which the time of interest and the tracking point are set in the M mode image. Since, on the display screen used when the time of interest is set, the B mode image at a set time is displayed in real time, it is possible to check noise conditions.

Moreover, the examiner operates the input portion 501 to input the maximum blood pressure and the minimum blood pressure measured with the cuff-type blood pressure meter (step S09). These blood pressure values are utilized as the contracting period blood pressure Ps and the expanding period blood pressure Pd. In response to this, the elastic characteristic calculation portion 507 tracks, from the set tracking point, a brightness variation point characterizing the intima-vascular lumen boundary to perform the tracking. The tracking can be performed by various methods such as a tomographic image pattern matching method, a zero cross point method, a tissue Doppler method and a phase difference tracking method with the subject point being defined; it is needless to say that any method may be employed.

During the tracking of the specified region, the elastic characteristic calculation portion 507 determines the systolic maximum blood vessel diameter Ds and the diastolic minimum blood vessel diameter Dd shown in FIG. 5 to calculate the stiffness parameter β from the following equation:

$$\beta = [\mathrm{Log}(Ps/Pd)]/(Ds/Dd - 1)$$

The calculation result of the stiffness parameter β is displayed near the M mode image in the display screen (step S10).

Figure 32:
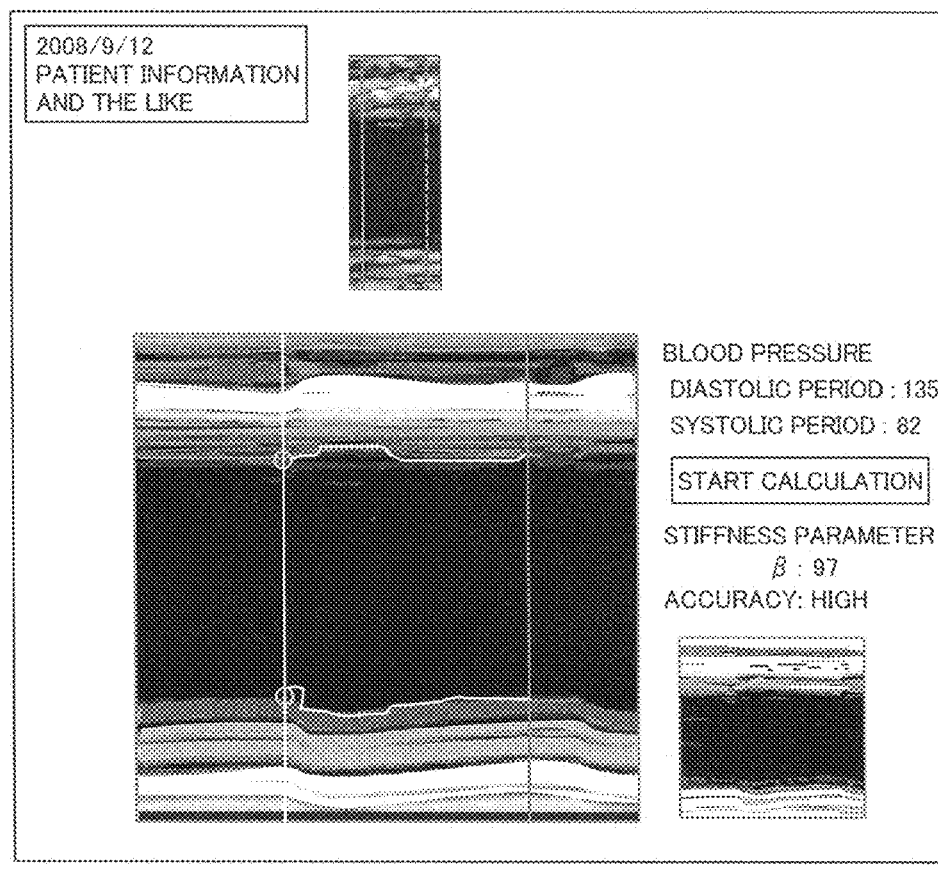
FIG. 32 is a display screen displaying the stiffness parameter by inputting a systolic blood pressure Ps and a diastolic blood pressure Pd.

FIG. 32 shows a display screen in which the stiffness parameter β is displayed by inputting the systolic blood pressure Ps and the diastolic blood pressure Pd. In the M mode image, paths are displayed that are produced by tracking the intima-vascular lumen boundary on the front wall and the rear wall of a blood vessel. The input blood presser and the calculated stiffness parameter β are displayed in values. In addition, a display is displayed which indicates that the displayed stiffness parameter β is calculated from an image in which no hand shake or body shake occurs and thus is a highly accurate elastic characteristic. A low reliable stiffness parameter β calculated from an image in which the hand shake or the body shake occurs may fail to be displayed, and, along with information on the accuracy, a low reliable stiffness parameter β may be displayed.

Figure 33:
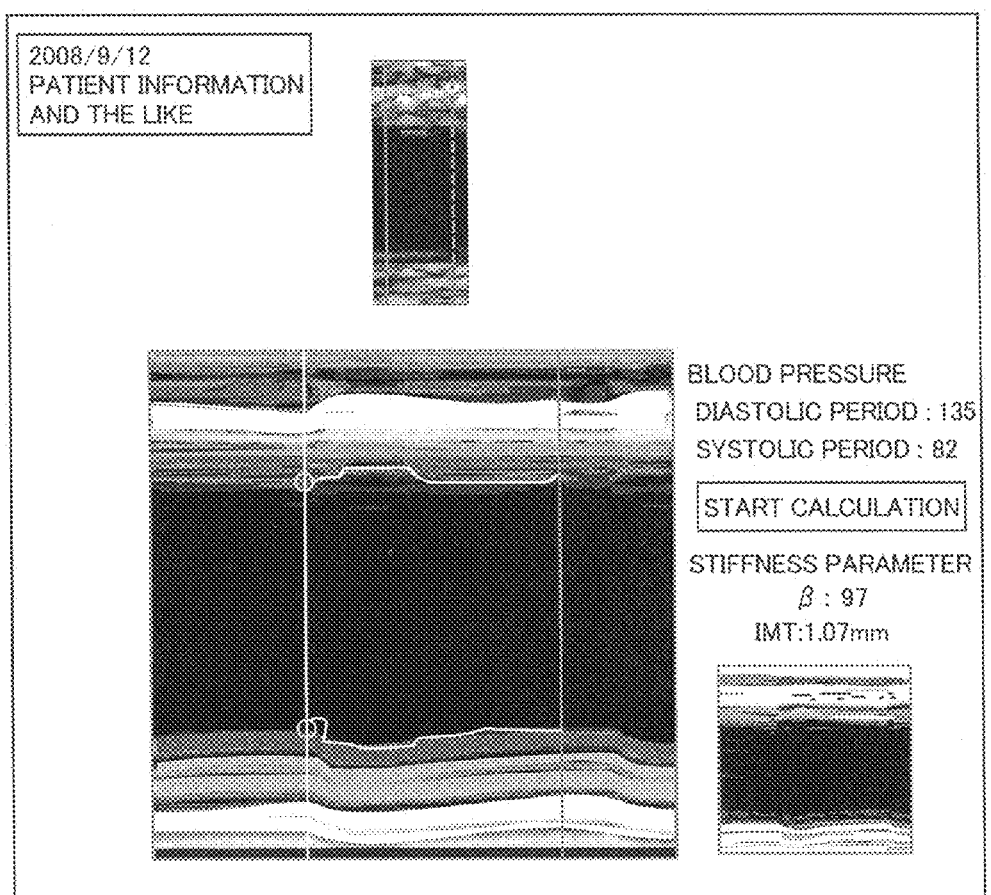
FIG. 33 is a diagram showing an example of a display screen in which the value of the IMT determined from information on a tracking portion at the time of interest shown along with the M mode image is additionally displayed.

By the use of information on the set tracking portion, the IMT (intima media thickness), the blood vessel diameter, the ratio between the minimum blood vessel diameter and the maximum blood vessel diameter and the like may be calculated and displayed on the display portion together with the elastic characteristics. FIG. 33 shows an example of a display screen in which an IMT value determined from the information on the tracking portion at the time of interest shown together with the M mode image is additionally written.

With the ultrasonic diagnostic device of the present invention, by reliably eliminating an M mode image including hand shake or body shake to calculate an elastic characteristic, it is possible to prevent a less accurate elastic characteristic result from being obtained. Thus, it is possible to stably and reliably obtain a high accurate elastic characteristic result.

In other words, since highly accurate measurement is required in elastic characteristics, and they are highly likely to be affected by noises, information on the accuracy of the elastic characteristics is important. With the present invention, in the first stage, an examiner can consciously eliminate the elastic characteristic in which there are problems in the measurement method or the like and the accuracy thereof.

According to the present invention, it is possible for an examiner such as a doctor to determine, before starting tracking for calculating an elastic characteristic in an ultrasonic diagnostic device, whether or not a reliable elastic characteristic can be obtained from data and to select an appropriate data portion. With the ultrasonic diagnostic device of the present invention, since elastic characteristics such as a high accurate elastic modulus can be stably acquired, it is possible to obtain a more reliable result than conventionally obtained.

Although, in the ultrasonic diagnostic device of this embodiment, one M mode image is selected, as the line of interest, from the M mode images equivalent to two lines, and the elastic characteristic is determined, highly continuous two or three lines are selected from about five candidate lines, and the elastic characteristic is calculated, and their average values may be used as the elastic characteristic of a blood vessel. In this case, five M mode images are displayed, and, among them, two or three M mode images are selected and the stiffness parameter β is determined. On an instruction screen, the stiffness parameter β of each of the M mode images and the stiffness parameter β determined by the averaging are displayed. Here, the stiffness parameter β in which the accuracy of the elastic characteristic is low is removed from the averaging calculation.

Although, in the ultrasonic diagnostic device of this embodiment, the stiffness parameter β is used as the elastic characteristic, a strain rate or an elastic modulus can be selected as the elastic characteristic. When the strain rate and the elastic modulus are calculated, since the thickness of a blood vessel wall, especially IMT (intima media thickness), is an issue, as shown in FIG. 3, the tracking point is set in the following four locations: a boundary between an adventitia and a media in a blood vessel front wall, a boundary between an intima and a vascular lumen in the blood vessel front wall, a boundary between the vascular lumen and the intima in a blood vessel rear wall and a boundary between the media and the adventitia in the blood vessel rear wall. Minute variations in blood vessel thickness are measured from the measurement values obtained by tracking the adventitia-media boundary and the intima-vascular lumen boundary in each of the front wall and the rear wall, and thus the maximum value Td and the minimum value Ts of the blood vessel thickness are determined.

By using these values, the strain rate can be determined from "(Td−Ts)/Td." The elastic modulus E can be determined from "E=(Ps−Pd)/[(Td−Ts)/Td]." When a more advanced algorism is used, the area between the adventitia-media boundary and the intima-vascular lumen boundary in each of the front wall and the rear wall is further divided into a plurality of pieces, and the elastic modulus of each region may be measured. The elastic characteristic calculation portion 507 calculates, for the set tracking portion, at least one of the IMT, the blood vessel diameter and the ratio of the minimum blood vessel diameter to the maximum blood vessel diameter, and the result may be displayed on the display 505 together with the elastic indices.

Although, in the ultrasonic diagnostic device of this embodiment, the position information is displayed on the horizontal axis in the M mode image, speed information may be displayed. In this case, it is preferable to set the tracking point on the B mode image or to together display the M mode image including the position information to set the tracking point.

Figure 34:
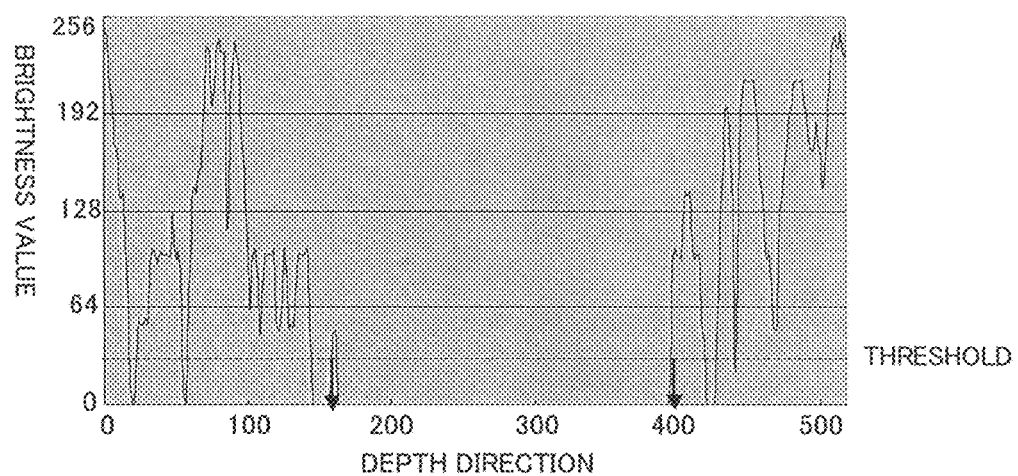
FIG. 34 is a diagram showing a brightness profile in the depth direction of a reception data at the time of interest set in FIG. 31.

The setting of the tracking point can be automatically performed by the use of brightness profile at the time of interest selected in the M mode image. FIG. 34 shows brightness profile at the time of interest set in FIG. 31 in the depth direction of the reception data. The left edge of the figure is the position of a probe; it is deeper as it extends rightward.

Moreover, in this embodiment, as in the fourth embodiment, as shown in FIG. 24, the vascular lumen-blood vessel front wall boundary to be selected as the tracing point can be determined at the point at which, when it is followed from the position of the vascular lumen detected as a black-removed portion of the center portion toward the direction of the probe, the brightness exceeds a threshold, further exceeds the top portion and then reaches the threshold. On the other hand, the vascular lumen-blood vessel rear wall boundary can be determined at the point at which, when it is followed from the center portion toward the direction of the deeper portion, the brightness reaches the threshold. Although, in the figure, the same threshold is used, the front wall boundary and the rear wall boundary may be determined with different thresholds.

Sixth Embodiment

Figures 35A, 35B:
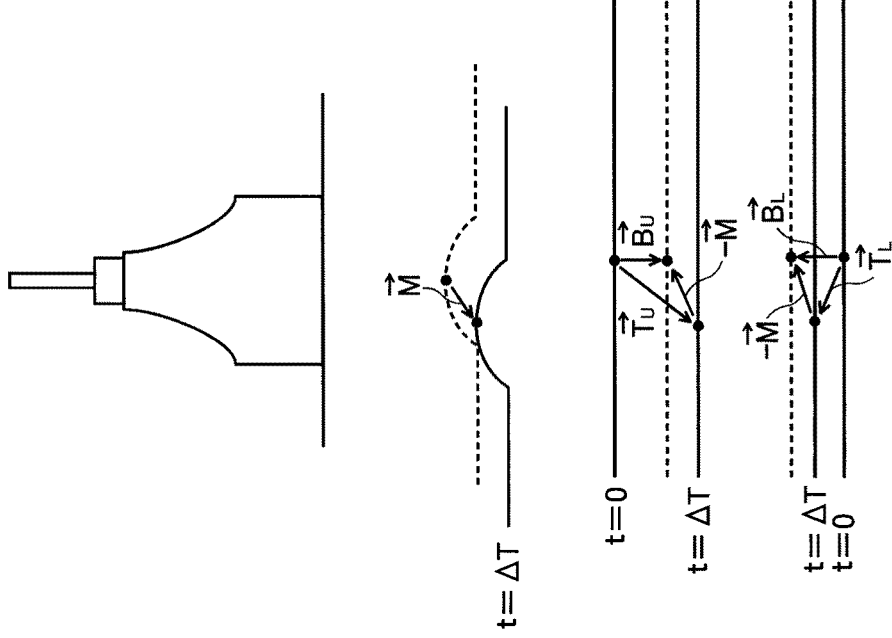
FIGS. 35A and 35B are schematic diagrams showing a method of correcting hand shake or body shake in an ultrasonic diagnostic device according to a sixth embodiment of the present invention.
Figure 36:
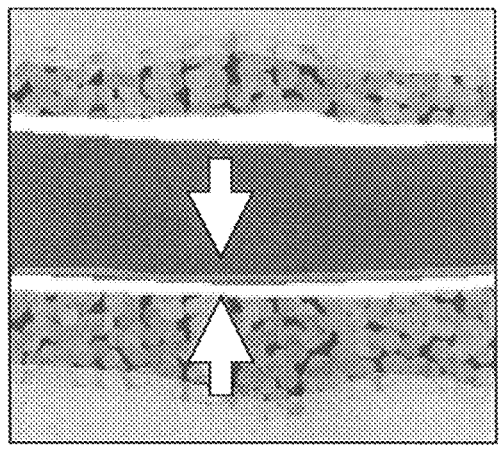
FIG. 36 is a diagram showing an example of an ultrasonic image showing a blood vessel wall at a normal state.
Figure 37:
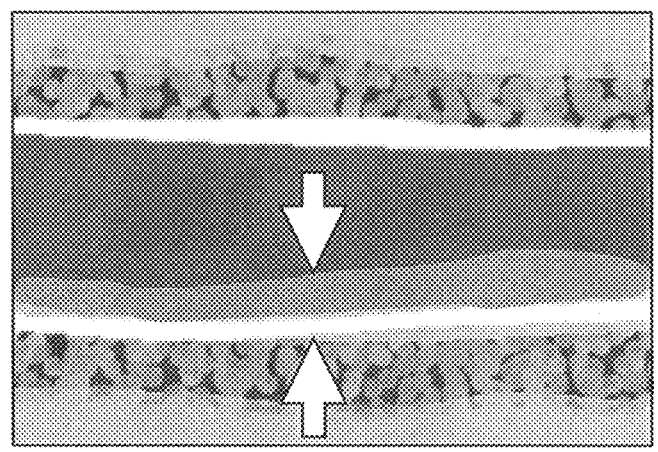
FIG. 37 is a diagram showing an example of an ultrasonic image showing a blood vessel wall whose membrane thickness is larger by plaque.
Figure 38:
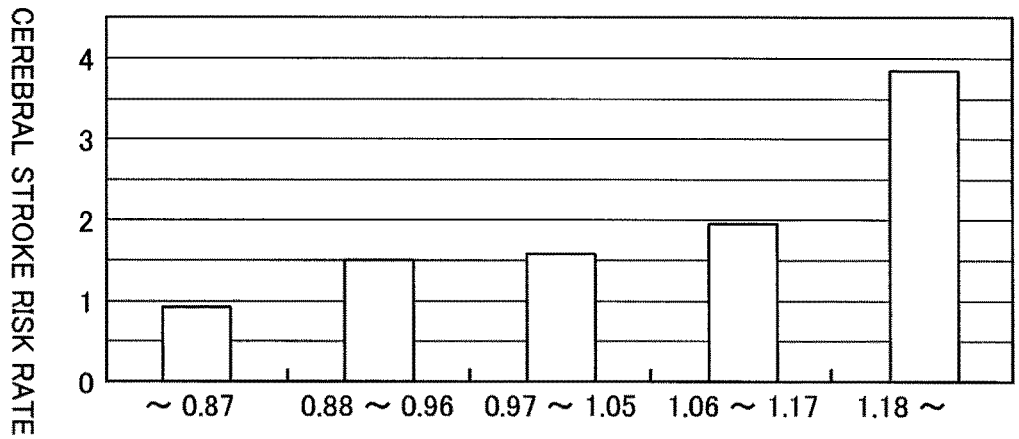
FIG. 38 is a graph showing the relationship between the IMT and a cerebral accident risk ratio.
Figure 39:
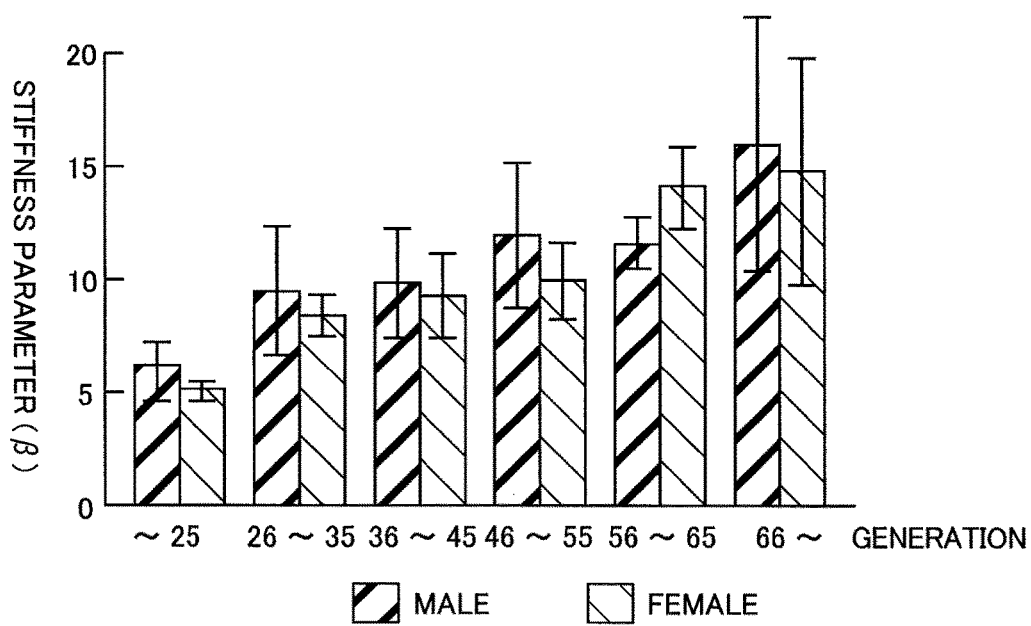
FIG. 39 is a graph showing variations in stiffness parameter β on an age-by-age basis.
Figure 40:
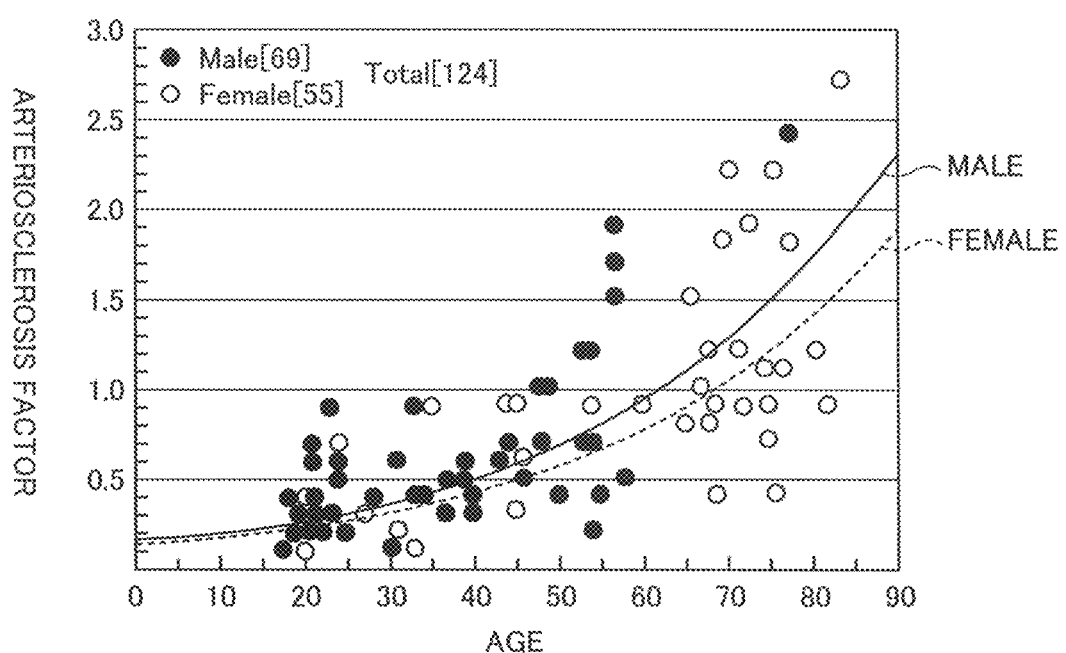
FIG. 40 is a graph showing the correlation between arteriosclerosis factors representing the mechanical characteristic of an artery and ages.
Figure 41:
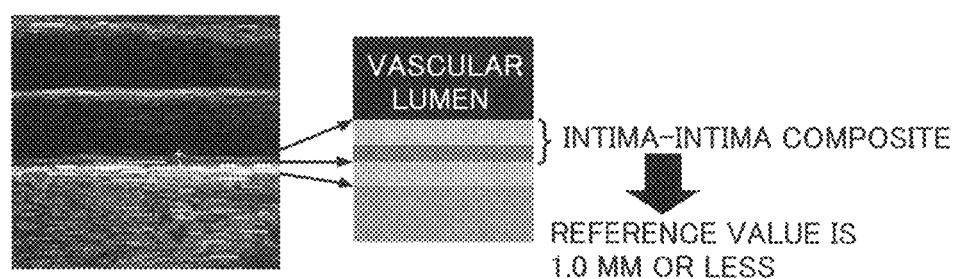
FIG. 41 is a diagram showing an ultrasonic image of a carotid artery.
Figure 42A:
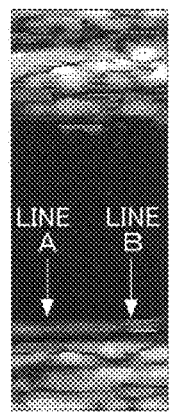
FIGS. 42A and 42B are diagrams showing B mode images obtained by measuring minute variations in a carotid artery blood vessel wall.
Figure 42B:
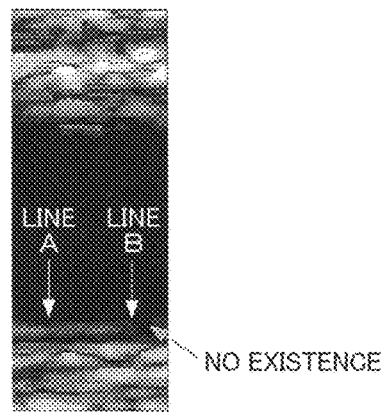
Figure 43A:
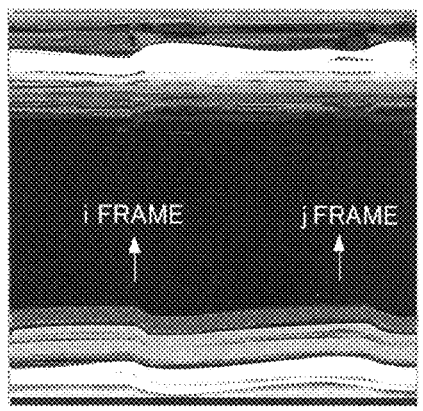
FIGS. 43A and 43B are diagrams showing M mode images obtained by measuring minute variations in the carotid artery blood vessel wall.
Figure 43B:
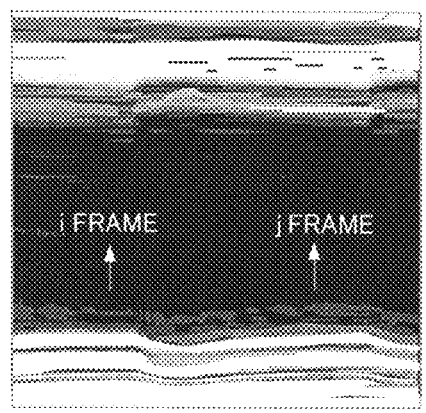
Figure 44:
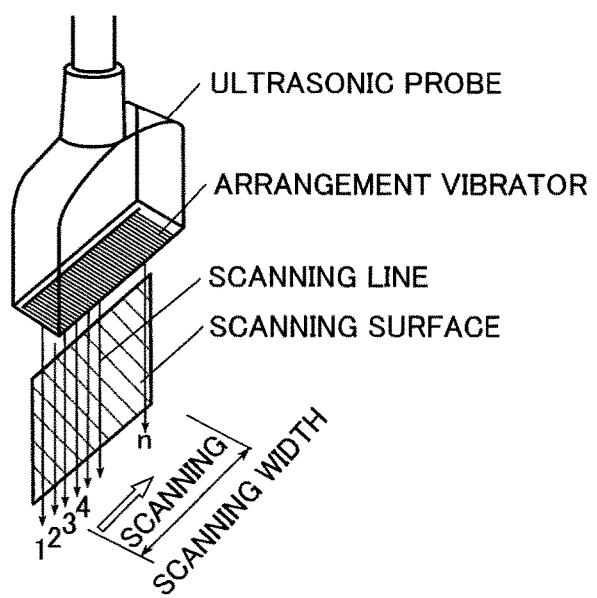
FIG. 44 is a schematic diagram showing the configuration of an ultrasonic probe.

FIGS. 35A and 35B are schematic diagrams showing a method of correcting hand shake or body shake in an ultrasonic diagnostic device according to a sixth embodiment of the present invention.

Whereas, in the fifth embodiment, the reception data excluding the hand shake or the body shake is used, and thus the elastic characteristics are calculated, in the sixth embodiment, reception data in which, in the reception data including the hand shake or the body shake, the amount of hand shake or body shake is corrected is used, and thus the elastic characteristics are calculated. The fifth embodiment is similar to the sixth embodiment except this point, and thus the description of like parts will not be repeated and different parts will only be described.

In this embodiment, when the beat involving hand shake/body shake determination portion 506 shown in FIG. 25 determines that the hand shake or the body shake occurs, the following correction is performed.

As shown in FIGS. 35A and 35B, a blood vessel diameter at a time t=0 corresponds to the systolic maximum blood vessel diameter Ds shown in FIG. 5; a blood vessel diameter at a time t=ΔT corresponds to the diastolic minimum blood vessel diameter Dd shown in FIG. 5. FIG. 35A shows a state in which there is no hand shake or body shake at the time t=ΔT; FIG. 35B shows a state in which the hand shake or the body shake is present at the time t=ΔT.

When the stiffness parameter β is calculated, as shown in FIG. 35B, at the time t=ΔT, the amount of shake M in the hand shake or the body shake serving as the amount of displacement of the relative position between the ultrasonic probe 101 and the body under test and tracking vector $T_U$ and $T_L$ are determined by the pattern matching or the like. Pulse vectors $B_U$ and $B_L$ are determined by an equation "B=T−M." The pulse vectors $B_U$ and $B_L$ determined, in this way, by subtracting the amount of shake M from the amount of displacement of a body tissue are those in which the amount of shake M in the hand shake or the body shake are corrected, and correspond to FIG. 35A in which no hand shake or body shake occurs.

Since the ultrasonic diagnostic device tends to have more difficulties in detecting the blood vessel front wall than the blood vessel rear wall, it is assumed that $B_U=B_L$, and the above correction is performed on only $B_L$, with the result that the pulse vectors $B_U$ and $B_L$ may be determined.

According to the sixth embodiment, since, in the M mode image including the hand shake or the body shake, the amount of shake in the hand shake or the body shake is corrected, and thus elastic characteristics are calculated, it is possible to stably and reliably obtain highly accurate elastic characteristics even if the hand shake or the like occurs.

INDUSTRIAL APPLICABILITY

In the present invention, with the ultrasonic diagnostic device that transmits ultrasound to the body under test and that receives ultrasonic echo reflected off the body under test to generate the ultrasonic image data and that measures the IMT of a blood vessel, it is possible to accurately and highly recognizably notify a person to be tested of arteriosclerosis risk.

According to the present invention, there is provided an ultrasonic diagnostic device that allows an examiner to visually and easily understand the movement state of the subject region to be tested by including, in the ultrasonic diagnostic device that transmits ultrasound to the body under test and that receives ultrasonic echo reflected off the body under test to generate the ultrasonic image data, a feature in which, in a three-dimensional coordinate system including the time axis, measurement results based on the ultrasonic image are displayed.

According to the present invention, there is provided an ultrasonic diagnostic device that reliably obtains stable elastic indices because, in the ultrasonic diagnostic device that transmits ultrasound to the body under test and that receives ultrasonic echo from the body under test to generate the ultrasonic image data, the stable data region can be selected and specified from the image data displayed on the display.

According to the present invention, there is provided an ultrasonic diagnostic device that can measure an elastic index in which unstable data is reliably eliminated from the ultrasonic image information obtained by detecting the hand shake or the body shake in the ultrasonic diagnostic device that transmits ultrasound to the body under test and that receives ultrasonic echo from the body under test to generate the ultrasonic image data.

DESCRIPTION OF SYMBOLS 101 ultrasonic probe
103 blood pressure meter
105 display
107 arteriosclerosis risk comparison information
111 transmit/receive control portion
113 transmission circuit
115 reception circuit
117 tomographic image formation portion
119 display processing portion
121 IMT measurement line setting portion
123 IMT calculation portion
125 measurement tracking portion
127 blood vessel wall displacement calculation portion
129 blood pressure measurement portion
131 β calculation portion
132 elastic modulus calculation portion
133 arteriosclerosis risk determination portion
217 image data generation portion
219 image storage device
221 display processing portion
223 display device
225 subject setting portion
227 position identification portion
401 input portion
407 display
411 system control portion
413 reception data memory
415 image generation portion
417 elastic index calculation portion
421 image processor
423 display processing portion
501 input portion
504 hand shake/body shake detection portion
505 display
506 beat involving hand shake/body shake determination portion
507 elastic characteristic calculation portion
511 system control portion
513 reception data memory
517 tomographic image formation portion
519 display processing portion
521 image processor
601 area between ultrasonic probe and a blood vessel
602 blood vessel
603 blood vessel front wall
604 vascular lumen
605 blood vessel rear wall

The invention claimed is:

1. An ultrasonic diagnostic device comprising:
an ultrasonic probe including a plurality of ultrasonic transducers transmitting and receiving ultrasound to and from a living body tissue moving in synchronization with a pulse of a body under test;
a transmission circuit configured to supply a plurality of drive signals to said ultrasonic probe;
a reception circuit configured to process a plurality of reception signals output from said ultrasonic probe to generate reception data;
a memory configured to store said reception data generated by said reception circuit; and
a central processing unit configured to execute software instructions; wherein the software instructions instruct the central processing unit to:
generate B-mode image data representing a B-mode image of said living body tissue and M-mode image data representing at least one M-mode image showing temporal changes of said living body tissue for a predetermined period on at least one line of interest set in said B-mode image, based on said reception data stored in said memory;
detect an amount of change of a relative position between said ultrasonic probe and said body under test in said reception data corresponding to said at least one M-mode image for said predetermined period;
determine whether at least one of hand movement and body movement occurs or not in said reception data corresponding to said at least one M-mode image for said predetermined period, based on said amount of change of said relative position;
display said at least one M-mode image together with information indicating whether the at least one of hand movement and body movement occurs or not at any point of time shown in said at least one M-mode image for said predetermined period, on a screen of a display; and
measure a displacement magnitude of said living body tissue in said reception data corresponding to at least one M-mode image in which hand movement and body movement do not occur while eliminating any M-mode image in which at least one of hand movement and body movement occurs, and calculate an elastic characteristic of an area within said living body tissue by using said displacement magnitude.

2. The ultrasonic diagnostic device of claim 1, wherein said central processing unit is instructed to detect said amount of change of said relative position in said reception data obtained from said living body tissue between (i) said ultrasonic probe which is pressed onto said body under test and (ii) said area of which said elastic characteristic is calculated.

3. The ultrasonic diagnostic device of claim 1, wherein said central processing unit is instructed to determine that the at least one of hand movement and body movement occurs in a case where said amount of change of said relative position is larger than a threshold value.

4. The ultrasonic diagnostic device of claim 3, wherein said threshold value for said amount of change of said relative position is not less than 0.1 mm.

5. The ultrasonic diagnostic device of claim 1, wherein said central processing unit is instructed to detect said amount of change of said relative position by one of calculation of difference between frames of said at least one M-mode image and pattern matching between frames of said at least one M-mode image.

6. The ultrasonic diagnostic device of claim 1, wherein said central processing unit is instructed to calculate, as said elastic characteristic, at least one of a stiffness parameter $\beta$, a strain rate, and an elastic modulus.

7. The ultrasonic diagnostic device of claim 1, wherein said living body tissue is any one of a blood vessel, a heart, and a carotid artery.

8. The ultrasonic diagnostic device of claim 1, wherein said central processing unit is instructed to subtract said amount of change of said relative position from said displacement magnitude of said living body tissue to correct said displacement magnitude of said living body tissue, and calculate said elastic characteristic by using the corrected displacement magnitude of said living body tissue.

* * * * *